(12) United States Patent
Grundy et al.

(10) Patent No.: US 6,991,810 B1
(45) Date of Patent: Jan. 31, 2006

(54) PRODUCT FROM STARFISH

(75) Inventors: Michelle Marguerite Grundy, Colebrook (GB); John Douglas McKenzie, Scotland (GB); Neville Vincent Richardson, Fife (GB); Charles Daniel Bavington, Oban (GB); Barbara Mulloy, London (GB); Rebecca Lever, London (GB); Clive Pete Page, London (GB)

(73) Assignee: King's College London, London (GB)

( * ) Notice: Subject to any disclaimer, the term of this patent is extended or adjusted under 35 U.S.C. 154(b) by 80 days.

(21) Appl. No.: 10/018,240

(22) PCT Filed: Jun. 8, 2000

(86) PCT No.: PCT/GB00/02233

§ 371 (c)(1),
(2), (4) Date: Apr. 8, 2002

(87) PCT Pub. No.: WO00/75183

PCT Pub. Date: Dec. 14, 2000

(30) Foreign Application Priority Data

Jun. 8, 1999 (GB) ................................. 9913237

(51) Int. Cl.
*A61K 35/12* (2006.01)
*A61K 35/16* (2006.01)

(52) U.S. Cl. .......................................... 424/573; 514/8
(58) Field of Classification Search ................... 514/8; 424/573

See application file for complete search history.

(56) References Cited

U.S. PATENT DOCUMENTS 5,674,853 A 10/1997 Forse et al.
5,695,552 A 12/1997 Taylor

FOREIGN PATENT DOCUMENTS

DE 196 46 324 5/1997

OTHER PUBLICATIONS

Grundy, M.M., et al., 2nd US/Pacific Rim Workshop on Emerging Non-Metallic Materials, 1999, abst. 79, www.dsto.defence.gov.au/corporate/conferences/icmcf/fullabstractsA-K.html#79.
Sousa, M., et al., Biological Blletin (Woods Hole) 185 215-224 (1993), abstract Souza-Santos, H., and Sasso, W.S., Experientia 29: 473-474 (1993).

*Primary Examiner*—Herbert J. Lilling
(74) *Attorney, Agent, or Firm*—St. Onge Steward Johnston & Reens LLC

(57) ABSTRACT

The invention relates to a product capable of having one or more properties sected from: anti-fouling properties, anti-adhesive properties, anti-inflammatory properties, and wherein said product is obtainable from starfish.

7 Claims, 6 Drawing Sheets

| "FMLP" | N/S | 0mcg/ml | 0.1mcg/ml | 1mcg/ml | 10mcg/ml | 100mcg/ml | POT |
|---|---|---|---|---|---|---|---|
| A | 93 | 241 | 248 | 268 | 242 | 180 | 1305 |
|   | 93 | 276 | 321 | 308 | 258 | 215 | 1146 |
|   | 105 | 290 | 264 | 317 | 268 | 143 | 1132 |
| B | 133 | 494 | 478 | 522 | 465 | 401 | 1971 |
|   | 177 | 475 | 557 | 573 | 476 | 401 | 1860 |
|   | 167 | 535 | 484 | 548 | 457 | 418 | 1934 |
| C | 114 | 347 | 322 | 369 | 315 | 249 | 1288 |
|   | 135 | 361 | 370 | 295 | 269 | 316 | 1203 |
|   | 125 | 228 | 237 | 259 | 281 | 261 | 1197 |
| A%adh | 7.126437 | 18.46743 | 19.003831 | 20.5364 | 18.54406 | 13.793103 | |
|   | 8.115183 | 24.08377 | 28.010471 | 26.87609 | 22.51309 | 18.760908 | |
|   | 9.275618 | 25.61837 | 23.321555 | 28.00353 | 23.67491 | 12.632509 | |
| B%adh | 6.747844 | 25.06342 | 24.251649 | 26.48402 | 23.59209 | 20.345003 | |
|   | 9.516129 | 25.53763 | 29.946237 | 30.80645 | 25.5914 | 21.55914 | |
|   | 8.634953 | 27.66287 | 25.025853 | 28.33506 | 23.62978 | 21.613237 | |
| C%adh | 8.850932 | 26.94099 | 25 | 28.64907 | 24.45652 | 19.332298 | |
|   | 11.22195 | 30.00831 | 30.756442 | 24.52203 | 22.36076 | 26.267664 | |
|   | 10.44277 | 19.04762 | 19.799499 | 21.63743 | 23.47536 | 21.804511 | |
| A%spad | 0 | 11.341 | 11.877395 | 13.40996 | 11.41762 | 6.6666667 | |
|   | 0 | 15.96859 | 19.895288 | 18.76091 | 14.39791 | 10.645724 | |
|   | 0 | 16.34276 | 14.045936 | 18.72792 | 14.39929 | 3.3568905 | |
| B%spad | 0 | 18.31558 | 17.503805 | 19.73617 | 16.84424 | 13.597159 | |
|   | 0 | 16.02151 | 20.430108 | 21.29032 | 16.07527 | 12.043011 | |
|   | 0 | 19.02792 | 16.3909 | 19.7001 | 14.99483 | 12.978283 | |
| C%spad | 0 | 18.09006 | 16.149068 | 19.79814 | 15.60559 | 10.481366 | |
|   | 0 | 18.78637 | 19.534497 | 13.30008 | 11.13882 | 15.045719 | |
|   | 0 | 8.604845 | 9.3567251 | 11.19465 | 13.03258 | 11.361738 | |
| Amean | 0 | 14.55078 | 15.272873 | 16.96626 | 13.40494 | 6.8897605 | |
| Bmean | 0 | 17.78833 | 18.108271 | 20.2422 | 15.97145 | 12.872818 | |
| Cmean | 0 | 15.16042 | 15.01343 | 14.76429 | 13.259 | 12.296274 | |
| A%control |   | 100 | 104.96258 | 116.6004 | 92.12524 | 47.349769 | |
| B%control |   | 100 | 101.79858 | 113.7948 | 89.78607 | 72.366628 | |
| C%control |   | 100 | 99.030404 | 97.38705 | 87.45795 | 81.107716 | |
| mean |   | 100 | 101.93052 | 109.2607 | 89.78976 | 66.941371 | |
| sd |   | 0 | 2.9682857 | 10.37816 | 2.333649 | 17.520697 | |
| sem |   | 0 | 1.7137405 | 5.991831 | 1.347333 | 10.115579 | |
| A%inhib |   | 0 | -4.962575 | -16.60036 | 7.874756 | 52.650231 | |
| B%inhib |   | 0 | -1.798575 | -13.7948 | 10.21393 | 27.633372 | |
| C%inhib |   | 0 | 0.9695955 | 2.612948 | 12.54205 | 18.892284 | |
| mean |   | 0 | -1.930518 | -9.260739 | 10.21024 | 33.058629 | |
| sd |   | 0 | 2.9682857 | 10.37816 | 2.333649 | 17.520697 | |
| sem |   | 0 | 1.7137405 | 5.991831 | 1.347333 | 10.115579 | |

FIG. 5

| "IL-1β" | N/S | 0mcg/ml | 0.1mcg/ml | 1mcg/ml | 10mcg/ml | 100mcg/ml | POT |
|---|---|---|---|---|---|---|---|
| A | 115 | 216 | 136 | 171 | 188 | 134 | 1305 |
|  | 99 | 181 | 193 | 226 | 155 | 177 | 1146 |
|  | 96 | 166 | 214 | 204 | 138 | 146 | 1132 |
| B | 167 | 272 | 438 | 433 | 324 | 409 | 1971 |
|  | 162 | 351 | 447 | 496 | 291 | 312 | 1860 |
|  | 184 | 264 | 334 | 471 | 286 | 308 | 1934 |
| C | 107 | 199 | 188 | 230 | 153 | 185 | 1288 |
|  | 128 | 177 | 145 | 180 | 144 | 186 | 1203 |
|  | 118 | 176 | 144 | 156 | 141 | 179 | 1197 |
| A%adh | 8.812261 | 16.55172 | 10.421456 | 13.10345 | 14.40613 | 10.268199 |  |
|  | 8.638743 | 15.79407 | 16.841187 | 19.72077 | 13.52531 | 15.445026 |  |
|  | 8.480565 | 14.66431 | 18.904594 | 18.0212 | 12.19081 | 12.897527 |  |
| B%adh | 8.472856 | 13.8001 | 22.222222 | 21.96854 | 16.43836 | 20.750888 |  |
|  | 8.709677 | 18.87097 | 24.032258 | 26.66667 | 15.64516 | 16.774194 |  |
|  | 9.513961 | 13.65047 | 17.269907 | 24.35367 | 14.788 | 15.925543 |  |
| C%adh | 8.307453 | 15.45031 | 14.596273 | 17.85714 | 11.87888 | 14.363354 |  |
|  | 10.64007 | 14.71322 | 12.0532 | 14.96259 | 11.97007 | 15.461347 |  |
|  | 9.857978 | 14.70343 | 12.030075 | 13.03258 | 11.77945 | 14.954052 |  |
| A%spad |  | 0 | 7.739464 | 1.6091954 | 4.291188 | 5.59387 | 1.4559387 |
|  |  | 0 | 7.155323 | 8.2024433 | 11.08202 | 4.886562 | 6.8062827 |
|  |  | 0 | 6.183746 | 10.424028 | 9.540636 | 3.710247 | 4.4169611 |
| B%spad |  | 0 | 5.327245 | 13.749366 | 13.49569 | 7.9655 | 12.278031 |
|  |  | 0 | 10.16129 | 15.322581 | 17.95699 | 6.935484 | 8.0645161 |
|  |  | 0 | 4.136505 | 7.7559462 | 14.83971 | 5.274043 | 6.4115822 |
| C%spad |  | 0 | 7.142857 | 6.2888199 | 9.549689 | 3.571429 | 6.0559006 |
|  |  | 0 | 4.07315 | 1.4131338 | 4.322527 | 1.330008 | 4.8212801 |
|  |  | 0 | 4.845447 | 2.1720969 | 3.174603 | 1.92147 | 5.0960735 |
| Amean |  | 0 | 7.026177 | 6.7452223 | 8.304616 | 4.730226 | 4.2263942 |
| Bmean |  | 0 | 6.54168 | 12.275964 | 15.4308 | 6.725009 | 8.9180433 |
| Cmean |  | 0 | 5.353818 | 3.2913502 | 5.682273 | 2.274302 | 5.3244181 |
| A%control |  |  | 100 | 96.00131 | 118.1954 | 67.3229 | 60.152114 |
| B%control |  |  | 100 | 187.65767 | 235.8843 | 102.8025 | 136.3265 |
| C%control |  |  | 100 | 61.47669 | 106.135 | 42.48001 | 99.450857 |
| mean |  |  | 100 | 115.04522 | 153.4049 | 70.86846 | 98.643156 |
| sd |  |  | 0 | 65.210527 | 71.68336 | 30.31713 | 38.093615 |
| sem |  |  | 0 | 37.649315 | 41.38641 | 17.5036 | 21.993359 |
| A%inhib |  |  | 0 | 3.9986897 | -18.19537 | 32.6771 | 39.847886 |
| B%inhib |  |  | 0 | -87.65767 | -135.8843 | -2.802476 | -36.326498 |
| C%inhib |  |  | 0 | 38.52331 | -6.134968 | 57.51999 | 0.5491425 |
| mean |  |  | 0 | -15.04522 | -53.40488 | 29.13154 | 1.3568436 |
| sd |  |  | 0 | 65.210527 | 71.68336 | 30.31713 | 38.093615 |
| sem |  |  | 0 | 37.649315 | 41.38641 | 17.5036 | 21.993359 |

FIG. 5 CONT'D

PRODUCT FROM STARFISH

CROSS-REFERENCES TO RELATED APPLICATIONS

This application claims priority benefit of PCT/GB00/02233, filed internationally 8 Jun. 2000, which designated the United States and claimed priority benefit of GB 9913237.5, filed 8 Jun. 1999. Subject matter in GB 9913237.5 was filed as provisional application Ser. No. 60/167,340 in the United States on 24 Nov. 1999.

The present invention relates to a novel product. In particular, the invention relates to a novel product which has a broad applicability. More in particular, the invention relates to a novel product and its use as an industrial component such as an antifoulant, or an anti-adhesive, or as a pharmaceutical component such as an anti-inflammatory agent.

Biofouling—the coating of surfaces by organic molecules or organisms—is a major problem, especially in damp or aquatic environments. Anti-fouling agents are required for many different applications, particularly for marine structures which are exposed to sea water flora and fauna. Mildew or fungus may grow on house paints and the like, utilizing the paint medium as a nutrient, or in some cases using the underlying substrate, such as wood, as the nutrient. This may cause damage to the painted surface or a deterioration in the appearance of the painted surface. Slime or algae may develop in water cooling towers if effective compounds for preventing their growth are not present. Anti-fouling agents are useful in combating these problems.

As discussed in U.S. Pat. No. 5,071,479 the growth of marine organisms on the submerged parts of a ship's hull is a particular problem. Such growth increases the frictional resistance of the hull to passage through water, leading to increased fuel consumption and/or a reduction in the speed of the ship. Marine growths accumulate so rapidly that the remedy of cleaning and repainting as required in dry-dock is generally considered too expensive. An alternative is to limit the extent of fouling by applying to the hull a paint incorporating anti-fouling agents. These prior art anti-fouling agents are usually biocides which are released from the surface of the paint over a period of time at a concentration lethal to marine organisms at the hull surface. The anti-fouling paint fails only when the concentration of biocide available at the paint surface falls below the lethal concentration, and with modern paints up to two years of useful life is expected.

An extremely widely used biocide, particularly in marine anti-foulants, is tributyl tin (TBT). However, there is a growing concern about the environmental effects caused by using such organic tin biocides at their present commercial levels as an anti-foulant active ingredient in coating compositions for aquatic (marine) applications. It has been shown that, due to the wide-spread use of tributyltin-type compounds in particular, at concentrations as high as 20% by weight in paints for ship hulls, the pollution of surrounding water due to leaching has reached such a level as to cause the degradation of mussel and shell organisms. This toxicity is clearly a problem with prior art antifoulants.

Furthermore, these polluting effects have been detected along the French-British coastline and a similar effect has been confirmed in U.S. and Far Eastern waters. Under the most recent regulatory restrictions, with limited exceptions, pleasure boats up to 25 meters long are no longer permitted to use anti-foulant paint containing high levels of tributyltin compounds.

There is clearly a desire to provide alternative antifoulants to TBT based compounds.

U.S. Pat. No. 4,297,137 discloses that the effects of an anti-fouling composition can be lengthened by moderating the release of the anti-fouling constituents. This document discloses anti-fouling paints comprising at least one substance toxic to marine organism uniformly incorporated into a discontinuous solid matrix which is insoluble in sea water and is dispersed in the paint. The matrix is at least partially formed from at least one substance which becomes soluble in sea water under the action of enzymes liberated by marine organisms and/or by bacteria in contact with the paint. Thus, when a marine organism becomes associated with the painted surface, the toxic substance is released and the organism's growth is inhibited. Similar to prior art disclosures, the toxic substances envisaged by U.S. Pat. No. 4,297,137 include the well known copper and tin based compounds, such as TBT. Clearly, even controlled release of such prior art compounds pollutes the environment, albeit at lower levels than uncontrolled release. Furthermore, as the toxic compounds are released from these prior art antifoulant paints, the effective life of the paint as an antifoulant is reduced, since once all the toxic compound has been released, the coating will no longer function as an antifoulant. This is a problem of such prior art antifoulant formulations.

Anti-inflammatory agents are useful to reduce inflammation, modulate allergic reactions, alleviate symptoms of asthma, treat conditions such as inflammatory bowel disease (e.g. Crohn's disease), ulcerative colitis, rhinitis, reumatoid arthritis, psoriasis, interstitial cystitis, and control toxic shocks, among other uses. Heparin is a prior art product known to posess a wide array of anti-inflammatory properties. Heparin, however, is also a known anti-coagulant, reducing the ability of the blood to clot. Clearly, the anti-coagulant properties of heparin may be problematic in its use as an anti-inflammatory agent.

The present invention seeks to overcome such difficulties.
Aspects of the present invention are set out in the claims and are described below.

SUMMARY OF THE INVENTION

In a first aspect, the invention relates to a product capable of having one or more properties selected from: anti-fouling properties; anti-adhesive properties; anti-inflammatory properties; and wherein said product is obtainable from starfish.

Typically, the product will be free of at least one component with which it is usually associated in its natural environment.

Preferably the product is substantially free of the components with which it is usually associated in its natural environment.

More preferably the product is isolated from the components with which it is usually associated in its natural environment.

The term product as used herein may refer to a molecule or a plurality of molecules. The product of the present invention may preferably be obtained from starfish as disclosed herein. Most preferably, the product of the present invention may be molecule(s) obtainable from the mucus secretions of starfish. Preferably the starfish is *Marthasterias glacialis*. The product will preferably be obtained from said mucus secretions by collecting said secretions, and removing the particulate matter by centrifugation. The product may then be advantageously purified by size exclusion chromatography, and even more preferably be further purified by ion exchange chromatography.

In a highly preferred embodiment, the product of the present invention may be a proteoglycan obtainable from the mucus secretions of *Marthasterias glacialis*.

A proteoglycan (PG) is any glycoprotein which comprises a polypeptide or protein core with one or more glycosaminoglycans (GAGs) bound to it. A glycosaminoglycan (GAG) is a polysaccharide which has a simple repeating disaccharide unit and can be highly charged due to the prescence of sulphate and carboxyl groups.

In the present specification "foulants" referred to by the terms "anti-foul(s)", "anti-fouling", and "anti-foulants" include molecules or other substances, or may include organisms which may reside and/or grow on the surface to be treated with the present composition. Such organisms may include micro-organisms such as bacteria, fungi, protozoa, algae or other micro-organism. The organism may be a marine organism. Said marine organism may be a barnacle or limpet or any other organism capable of adhering to a substrate or surface.

The surface may be the surface of an organism, such as a mammal. The surface may be endothelial, for example vascular endothelium, or may be epithelial, for example bladder epithelium. The surface may be the surface of a prosthetic, or of an artificial implant. 'Fouling' describes the adhesion of said substances or organisms to said surface(s).

Accordingly, anti-fouling properties will be any characterisics or abilities of a product to inhibit, reduce, reverse, prevent or otherwise interfere with, discourage or slow down the process of fouling.

Adhesion or adherence is used to describe the association, attatchment, sticking, binding or bonding of a substance or organism to a surface or substrate. Therefore, anti-adhesive properties will be any characterisics or abilities of a product to inhibit, reduce, reverse, prevent or otherwise interfere with, discourage or slow down the process of adhesion.

Inflammation is a complex phenomenon observed in many organisms in response to wounding, infection, allergic reaction, toxic shock or the prescence of many kinds of pathogen, as well as many other factors. When the organism is an animal, this often involves the migration of white blood cells to the site of inflammation, and cell-cell contacts or adhesion. Anti-inflammatory properties describe any abilities of an anti-inflammatory agent to reduce the symptoms or causes of inflammation. Preferably, the products of the present invention when used as anti-inflammatory agents may inhibit, reduce, reverse, prevent or otherwise interfere with, discourage or slow down the process of inflammation. More preferably, an anti-inflammatory property of a product according to the invention may refer to its ability to interfere with the adhesion of bacterial cells to mammalian cells, most preferably an anti-inflammatory property of a product according to the invention may refer to its ability to interfere with the adhesion of white blood cells such as leukocytes or neutrophils to endothelial cells such as vascular endothelium, or with epithelial cells such as bladder epithelium. However, it is to be understood that the anti-inflammatory properties are not necessarily limited to such activities.

Preferably, the product of the invention is obtainable from *Marthasterias glacialis*, more preferably said product is obtainable from the mucus secretions of *Marthasterias glacialis*.

Preferably, the product is a proteoglycan, or an active component thereof.

The term 'an active component' of the product of the present invention may refer to a purified fraction of the product. For example, if the product of the invention comprises a plurality of molecular species, an active component thereof may be a plurality of molecular species which is selected from the original mixture, or may be a single molecular species selected from said mixture. In other words, the active component may be a subset of the molecules which the product comprises. Furthermore, an 'active component' of the product as used herein may refer to a molecular sub-species of the original mixture. For example, if the product of the invention is a proteoglycan, an active component thereof may comprise the glycan chain(s) or part thereof, or may comprise the polypeptide entity or part thereof, or any combination of the two.

Thus, in one aspect the product may be a glycan, or an active component thereof. Preferably, the glycan of the product is capable of displaying gas chromatography peaks as shown in FIG. 4, and as described in Table 3 (See Example 2).

In addition, or in the alternative, said active component may be one or more sugars found in said secretion.

The active component will preferably retain the activity of the product according to the invention. Preferred methods for assessing the activities of the product according to the present invention are described herein and will be known to those skilled in the art. Preferably, the activities of the product of the present invention are anti-fouling properties, anti-adhesive properties, and anti-inflammatory properties. Preferably, the product of the present invention, or an active component thereof, will posess at least one of said properties, more preferably will posess at least two of said properties, and most preferably will posess at least all three of these properties.

Preferably, the product or active component thereof has one or more characteristics selected from:
i) a molecular weight of about 1.100 kDa as measured by 3% polyacrylamide gel electrophoresis
ii) capable of displaying a Fourier transform infra-red spectrum similar to that shown in FIG. 3, with the peaks indicated in Table 2
iii) capable of displaying a NMR proton spectrum similar to that shown in FIG. 1
iv) sensitivity to the action of chondroitinase ABC I
v) sensitivity to the action of N-glycanase
vi) resistance to the action of chondroitinases ACI and B
vii) resistance to the action of proteinase K
viii) resistance to the action of papain
ix) sensitivity to the action of neuraminidase The terms sensitivity/resistance as used herein are qualitative. Sensitivity/resistance may be esimated by exposing the product to the particular enzyme(s) of interest, and comparing the chromatographic profiles of product exposed to the enzyme(s) with the chromatographic profiles of product which has not been exposed to the enzyme(s). If the chromatographic profiles differ, then it would be inferred that the product exhibited sensitivity to the enzyme(s), whereas if the profiles were essentially the same, the product would be judged to be resistant to the enzyme(s). Further, sensitivity or resistance to a particular enzyme may be estimated in a similar manner by comparing the SDS-PAGE profiles of samples of product which had either been treated with enzyme, or had not been treated with enzyme. As explained above, a difference between the profiles would be taken to indicate sensitivity to the enzyme(s), whereas if the profiles were essentially the same, the product would be judged to be insensitive or resistant to the enzyme(s). Further explanation of these assessments can be found in Examples 1 and 2.

Preferably said product has two or more of said characteristics, more preferably three or more of said characteristics, more preferably four or more of said characteristics, even more preferably five or more of said characteristics, even more preferably six or more of said characteristics, yet more preferably seven or more of said characteristics, yet more preferably eight or more of said characteristics and most preferably all of said characteristics.

Preferred methods for assessing said characteristics may be found in the examples.

In a further embodiment, the product of the invention preferably will not have significant anti-coagulant properties. As used herein, significant anti-coagulant properties are anti-coagulant properties comparable to those of heparin. Any product having anti-coagulant properties less than those of heparin is considered not to have significant anti-coagulant properties.

Coagulation refers to the thickening or clotting of blood and assays for determination of coagulation or anti-coagulant properties are known in the art such as the Acuclot and Heptest diagnostic tests, or for example see Thompson and Harker 1983 (*Manual of Hemostasis and Thrombosis* Davis Company, Philadelphia).

In a further embodiment the invention relates to a method for the preparation of a product according to the present invention, said method comprising
i) collecting mucus from Marthasterias glacialis,
ii) removing particulate material by centrifugation
iii) subjecting the supernatent to column chromatography
iv) eluting the material from the chromatography column of (c), and
v) optionally dialysing said eluted material against distilled water.

The present invention also encompasses a method for preparing a pharmaceutical composition, said method comprising admixing a product of the present invention with a pharmaceutically acceptable carrier, diluent or excipient.

The present invention also encompasses a method for preparing an antifouling composition, said method comprising admixing a product of the present invention with a suitable vehicle, solvent, carrier, diluent or excipient.

The present invention also encompasses a method for preparing an anti-adhesive composition, said method comprising admixing a product of the present invention with a suitable vehicle, solvent, carrier, diluent or excipient.

The invention also relates to an antibody raised against the product according to the invention, or an antibody which has immunoreactivity with such a product, or a compound capable of having immunoreactivity with such an antibody.

DETAILED DESCRIPTION OF THE INVENTION

Typically, the product of the present invention is present in a composition.

The compositions of the present invention may be formulated as coatings, lacquers, stains, enamels and the like, hereinafter referred to generically as "coating(s)".

Thus, in one aspect the present invention provides a coating consisting of a composition as defined above.

The coating may include a liquid vehicle (solvent) for dissolving or suspending the composition.

The liquid vehicle may be selected from any liquid which does not interfere with the activities of any essential components of the composition. In particular, the liquid vehicle should not interfere with the activity of the anti-foulant compound. Suitable liquid vehicles are disclosed in (for example) U.S. Pat. No. 5,071,479 and include water and organic solvents including aliphatic hydrocarbons, aromatic hydrocarbons, such as xylene, toluene, mixtures of aliphatic and aromatic hydrocarbons having boiling points between 100 and 320° C., preferably between 150 and 230° C.; high aromatic petroleum distillates. e.g., solvent naptha, distilled tar oil and mixtures thereof; alcohols such as butanol, octanol and glycols; vegetable and mineral oils; ketones such as acetone; petroleum fractions such as mineral spirits and kerosene, chlorinated hydrocarbons, glycol esters, glycol ester ethers, derivatives and mixtures thereof.

The liquid vehicle may contain at least one polar solvent, such as water, in admixture with an oily or oil-like low-volatility organic solvent, such as the mixture of aromatic and aliphatic solvents found in white spirits, also commonly called mineral spirits.

The vehicle may typically contain at least one of a diluent, an emulsifier, a wetting agent, a dispersing agent or other surface active agent. Examples of suitable emulsifiers are disclosed in U.S. Pat. No. 5,071,479 and include nonylphenol-ethylene oxide ethers, polyoxyethylene sorbitol esters or polyoxyethylene sorbitan esters of fatty acids, derivatives and mixtures thereof.

Any suitable surface coating material may be incorporated in the composition and/or coating of the present invention. Examples of trade-recognized coating materials are polyvinyl chloride resins in a solvent based system, chlorinated rubbers in a solvent based system, acrylic resins and methacrylate resins in solvent based or aqueous systems, vinyl chloride-vinyl acetate copolymer systems as aqueous dispersions or solvent based systems, butadiene copolymers such as butadiene-styrene rubbers, butadiene-acrylonitrile rubbers, and butadiene-styrene-acrylonitrile rubbers, drying oils such as linseed oil, alkyd resins, asphalt, epoxy resins, urethane resins, polyester resins, phenolic resins, derivatives and mixtures thereof.

The composition and/or coating of the present invention may contain pigments selected from inorganic pigments, such as titanium dioxide, ferric oxide, silica, talc, or china clay, organic pigments such as carbon black or dyes, derivatives or mixtures thereof.

The composition or coating of the present invention may contain materials such as rosin to provide controlled release of the anti-foulant compound, rosin being to a very slight extent soluble in sea water.

The composition and/or coating of the present invention may contain plasticizers, rheology characteristic modifiers, other conventional ingredients or mixtures thereof.

The composition or coating of the present invention, particularly the coating, may further comprise an adjuvant conventionally employed in compositions used for protecting materials exposed to an aquatic environment. These adjuvants may be selected from additional fungicides, auxiliary solvents, processing additives such as defoamers, fixatives, plasticizers, UV-stabilizers or stability enhancers, water soluble or water insoluble dyes, colour pigments, siccatives, corrosion inhibitors, thickeners or anti-settlement agents such as carboxymethyl cellulose, polyarcylic acid or polymethacrylic acid, anti-skinning agents, derivatives or mixtures thereof.

The additional fungicide(s) used in the composition and/or coating of the present invention will preferably be soluble in the liquid vehicle.

Thus, in one aspect the present invention provides anti-foulant (such as a marine anti-foulant) comprising the product of the present invention.

Preferably, the anti-foulant is self-polishable.

The composition of the present invention can be provided as a ready-for-use product or as a concentrate. The ready-for-use product may be in the form of an aqueous solution, aqueous dispersion, oil solution, oil dispersion, emulsion, or an aerosol preparation.

The concentrate may be used, for example, as an additive for coating, or may be diluted prior to use with additional solvents or suspending agents.

An aerosol preparation according to the invention may be obtained by methods known to one skilled in the art by incorporating the composition of the present invention comprising or dissolved or suspended in, a suitable solvent, in a volatile liquid suitable for use as a propellant, for example the mixture of chlorine and fluorine derivatives of methane and ethane commercially available under the trademark "Freon", or compressed air, or other suitable propellant.

As discussed in U.S. Pat. No. 5,071,479 the composition or coating of the present invention may include additional ingredients known to be useful in preservatives or coatings. Such ingredients include fixatives such as carboxymethylcellulose, polyvinyl alcohol, paraffin, co-solvents, such as ethylglycol acetate and methoxypropyl acetate, plasticizers such as benzoic acid esters and phthlates, e.g., dibutyl phthalate, dioctyl phthalate and didodecyl phthalate, derivatives and mixtures thereof. Optionally dyes, color pigments, corrosion inhibitors, chemical stabilizers or siccatives (dryers) such as cobalt octate and cobalt naphthenate, may also be included depending on specific applications.

The composition or coating of the present invention can be applied by any of the techniques known in the art including brushing, spraying, roll coating, dipping or combinations thereof.

Compositions of the present invention can be prepared simply by mixing the various ingredients at a temperature at which they are not adversely affected. Equipment and methods conventionally employed in the manufacture of coating or similar compositions may be advantageously employed.

According to a further aspect, the invention relates to an antibody which is capable of reacting with the proteoglycan (PG) product described herein.

The antibody may be used to isolate further quantities of the product of the present invention and/or to detect the prescence of the product of the present invention.

The term "antibody", as used herein with reference to the present invention refers to a complete antibody or an antibody fragment or an antibody component, as well as any combination thereof, capable of binding to the selected target—namely the product of the present invention, or an active component thereof.

The term "antibody" refers to both conventionally produced antisera and monoclonal and engineered antibody molecules.

Antibody fragments and components include Fv, ScFv, dsFv, Fab, F(ab), Fab', F(ab)2, F(ab')2, Facb, monoclonal and polyclonal antibodies, engineered antibodies including chimeric, CDR-grafted antibodies, and artificially selected antibodies produced using phage display or alternative techniques. Small fragments, such Fv and ScFv, possess advantageous properties for analytical applications.

Preferably the antibody is linked to a detectable moiety.

Any suitable detectable moiety can used. The moiety can be directly detectable—such as a radiolabelled moiety, a moiety comprising a dye that is capable of producing a visually detectable signal (which need not necessarily be detectable by means of the naked eye) or a luminescent moiety. The moiety can be indirectly detectable—such as an enzyme moiety that is capable of acting on a substrate that is itself capable of generating a detectable signal or a moiety that is itself recognised by a labelled antibody.

The term "linked" includes direct attachment—such as through a direct bond, e.g. an ionic bond or a covalent bond.

Polyclonal antibodies (antisera) may be prepared by conventional means which comprise inoculating a host animal, for example a mouse, rat or a rabbit, with a polypeptide of the invention or peptide fragment thereof and recovering immune serum.

Techniques for the preparation of antibodies are discussed in, for example, Kohler and Milstein. (1975) Nature 256: 495–497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is also described in the above references and also in, for example, EP 0623679; EP 0368684 and EP 0436597, which are incorporated herein by reference.

By way of example, cell culture supernatants may be screened for the desired antibodies, preferably by immunofluorescent staining of the product according to the invention by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno) affinity chromatography, e.g. affinity chromatography with the product of the present invention.

As mentioned above, the present invention also covers pharmaceutical compositions comprising the products of the invention. In this regard, and in particular for human therapy, even though the products of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice.

By way of example, in the pharmaceutical compositions of the present invention, the products of the present invention may be admixed with any suitable binder(s), lubricant(s), suspending agent(s), coating agent(s), solubilising agent(s).

In general, a therapeutically effective daily oral or intravenous dose of the products of the invention is likely to range from 0.00001 to 500 mg/kg body weight of the subject to be treated, preferably 0.1 to 20 mg/kg. The products of the present invention may also be administered by intravenous infusion at a dose which is likely to range from 0.00001–1000 mg/kg/hr.

Tablets or capsules of the products may be administered singly or two or more at a time, as appropriate. It is also possible to administer the products in sustained release formulations.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the products of the invention can be administered by inhalation or in the form of a suppository or pessary, or they may be applied topically in the form of a lotion, solution, cream, ointment, foam (e.g. similar to Predfoam®), or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose or in capsules or ovules either alone or in admixture with excipients, or in the form of elixirs, solutions or suspensions containing flavouring or colouring agents.

The compositions (as well as the products alone) can also be injected parenterally, for example intracavernosally, intravenously, intramuscularly or subcutaneously. The compositions (as well as the products alone) may also be injected via the intrathecal/epidural routes. In this case, the compositions will comprise a suitable carrier or diluent.

For parenteral administration, the compositions are best used in the form of a sterile aqueous solution which may contain other substances, for example enough salts or monosaccharides to make the solution isotonic with blood. Said solutions may be used as an instillation (for example bladder, as in interstitial cystitis), or a rectal or vaginal wash, the salt/monosaccharide composition being adjusted accordingly to suitable levels for such applications.

For buccal or sublingual administration the compositions may be administered in the form of tablets or lozenges which can be formulated in a conventional manner.

For oral parenteral, buccal and sublingual administration to subjects (such as patients), the daily dosage level of the products of the present invention may typically be from 0.001 to 500 mg (in single or divided doses). Thus, and by way of example, tablets or capsules may contain from 0.001 to 500 mg of active product for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

Thus the invention provides a pharmaceutical composition comprising a product of the present invention, together with a pharmaceutically acceptable diluent, excipient or carrier.

The invention further provides a product of the present invention, or a pharmaceutical composition containing same, for use as a medicament. The medicament may be for human usage or veterinary usage.

The present invention will now be described by way of example, in which reference is made to:

FIG. 1 which shows a spectrum;

FIG. 2 which shows a spectrum;

FIG. 3 which shows a spectrum,

FIG. 4 which shows a spectrum; and

FIG. 5 which shows a table.

BRIEF DESCRIPTION OF THE FIGURES

In slightly more detail:

FIG. 5 shows a table of data illustrating inhibition of cellular adhesion by the product according to the invention.

EXAMPLE 1

Figure 1:
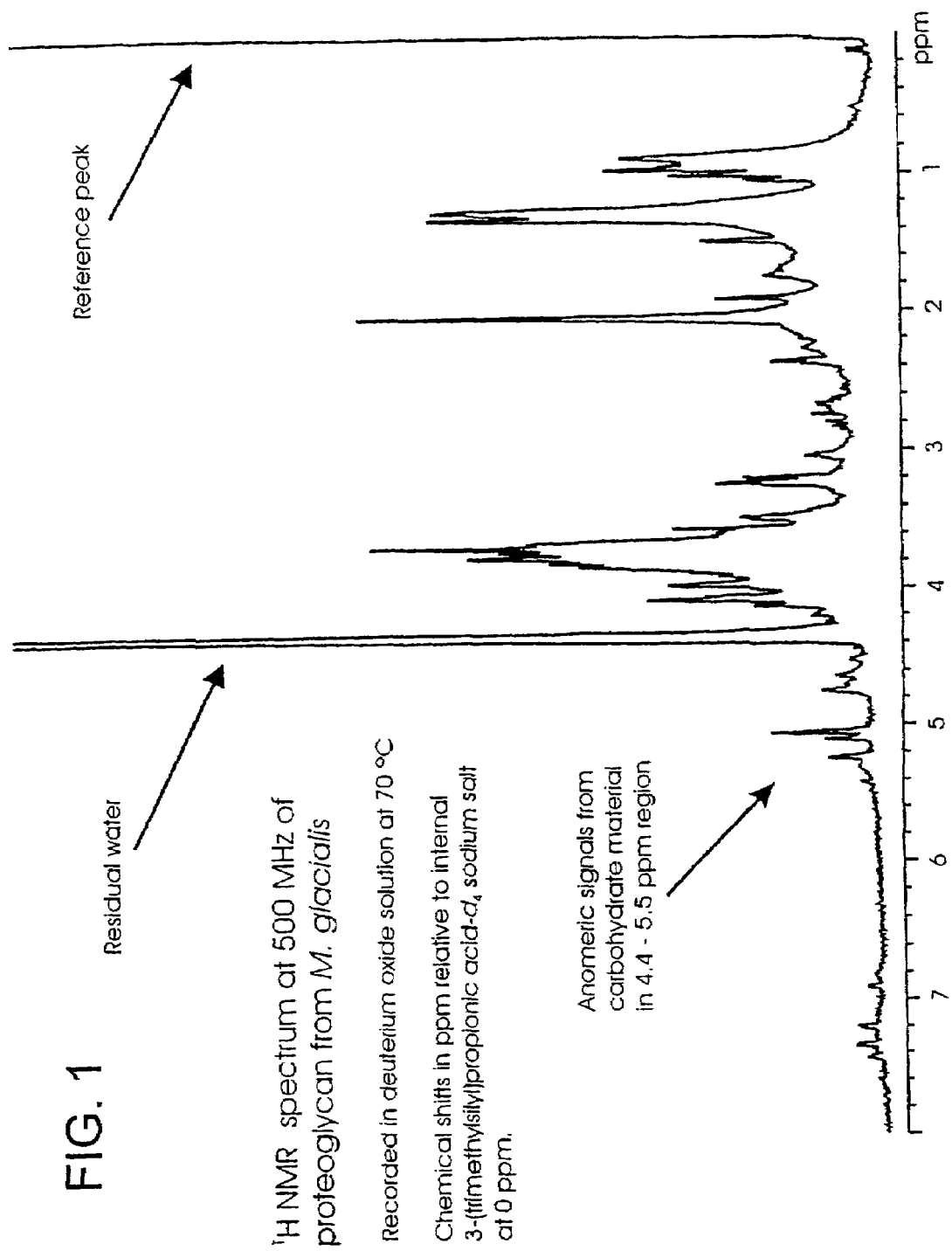
FIG. 1 shows an NMR proton spectrum of the proteoglycan product prepared as dscribed herein.

Collection and Purification of PROTEOGLYCAN (PG) PRODUCT

The starfish *Marthasterias glacialis* and *Porania pulvillus*, and the brittlestar *Ophiocomina nigra* are kept in through-flow seawater aquaria at a density of 20–40 animals per 500 liter tank.

Mucus is collected from *M. glacialis* and *O. nigra* in response to physical stress. Animals are first blotted with paper towels to remove excess seawater. Large amounts of mucus are secreted in response to agitation with a glass rod. Mucus is also collected from *M. glacialis* and *P. pulvillus* using suction. The mucus is aspirated from the dorsal surface of both species using a fine glass Pasteur pipette connected to a reservoir under suction.

Mucus collected by aspiration is a viscous acidic liquid. Stress mucus is less viscous and of lower pH (see table 1 below).

Size exclusion chromatography of mucus from all three species of echinoderm produces characteristic chromatograms.

Mucus samples are clarified by centrifugation at 500 g for 10 min and applied to a (95 cm long×26 mm diameter) column of Sepharose CL-6B (Pharmacia), which has previously been calibrated with high molecular weight standards. The absorbance of the eluant at 280 nm is monitored and fractions are collected. Protein content of samples is assayed using Coomassie® Plus reagent (Pierce). Glycosaminoglycan (GAG) content of fractions are assayed using the dye dimethyl methylene blue with heparin and chondroitin sulphate C as standards and as described below.

A major peak of GAG and protein elutes in the void volume, indicating the presence of a high molecular weight glycoprotein in all three mucus samples. The fractions from this peak are pooled for subsequent analysis/purification (see below).

The bulk of the glycoproteins present in the mucus elute in the void volume of the column. These glycoproteins are then dialysed against distilled $H_2O$ and freeze-dried. Reconstituted samples and PG standards are applied to a Q-Sepharose high performance column (Pharmacia) and eluted with a rising concentration of NaCl (0 to 1 M in 0.02M Tris-HCl buffer pH 8.0 over 10 minutes). The absorbance of the eluant at 280 nm is monitored and fractions are collected. Pooled fractions are dialysed against distilled $H_2O$ and freeze dried for long term storage at −20° C.

TABLE 1

Composition of echinoderm mucus

| | Volume (ml per animal) | pH | [protein] µg. ml$^{-1}$ | [GAG] µg. ml$^{-1}$ |
|---|---|---|---|---|
| M. glacialis-stress | 5 | 4.5 | 59 | 32 |
| M. glacialis-normal | 0.5 | 5 | 156 | 255 |
| P. pulvillus | 1 | 5 | 238 | 205 |
| O. nigra-stress | 0.5 | 4 | 57.4 | 18 |

Mucus secretions from *M. glacialis* contained an average of 210 µg/ml (+ or −78 µg/ml S.E.M.—Standard Error of the Mean; n=5) of proteoglycans.

EXAMPLE 2

Characterisation of PG Product

Molecular Weight

The Molecular Weight (MW) of the product is estimated by Sodium Dodecyl Sulphate-Polyacrylamide Gel Electrophoresis (SDS-PAGE) using 3% polyacrylamide gels. The MW is found to be approximately 1,100 kDa.

Susceptibility to Proteinases

Purified or semi-purified mucus glycoproteins are digested with proteinases (proteinase K and papain), neuramimidase, N-glycanase, and chondroitinases ACI, B, and ABC, and heparinases. The digests are analysed by ion-exchange chromatography using the Q-sepharose high performance column as described in Example 1. A change in the chromatographic profile indicates susceptibility to digestion.

The proteoglycan content of fractions collected from columns is estimated using the dimethylmethylene blue assay for sulphated GAGs as described in (Farndale et al., 1986: Biochem.Biophys.Acta vol 883, pp 171–177). Heparin and chondroitin sulphate C are used as standards.

The protein content of fractions collected from columns is measured using Coomassie® Plus reagent (Pierce) according to the manufacturer's instructions.

The uronic acid content of proteoglycans is determined after acid hydrolysis (6.0 M HCL at 100° C. for 6 h) by the modified carbazole reaction as described in (Bitter et al., 1962: Analytical Biochemistry vol 4, pp330–334), and the hexosamine content was determined by the Elson-Morgan reaction according to (Rondle et al., 1955: Biochem. J. vol 61, pp586–589).

The uronic acid content of the proteoglycan product is approximately 19 µg uronic acid per 1 mg PG. Similarly, the hexosamine content of the proteoglycan product is approximately 19 µg hexosamine per 1 mg PG. Radiolabelling indicates approximately 100 mol sulphate per mol GAG.

NMR Characterisation of PG Product

It is possible to obtain ID 500 MHz $^1$H NMR spectra of the mucus glycoproteins. It is possible to record a TOCSY spectrum at 70° C. from which spin systems can be deduced.

Samples are dissolved in 99.8% D$_2$O and transferred to 5 mm NMR tubes. Proton and carbon NMR spectra are recorded using a Varian Unity 500 NMR spectrometer, at temperatures of 45 or 70 degrees C.

FIG. 1 shows an NMR proton spectrum of the proteoglycan product prepared as described herein. This spectrum is recorded at 500 MHz, in D$_2$O solution, at 70° C. The numbers on the scale are parts per million (ppm) and are expressed relative to an internal standard compound, 3-(trimethylsilyl)propionic acid d$_4$ sodium salt. The peak from residual water is labelled, as are the reference peak, and the peaks in the spectrum most characteristic of the carbohydrate part of the molecule, the anomeric signals (ie those from the anomeric hydrogen, or H1, of each monosaccharide residue).

Signals attributable to both carbohydrate and peptide are present, and the distinctive acetyl methyl signal at 2.05 ppm is consistent with the high proportion of GalNAc and GlcNAc identified by monosaccharide analysis.

Anomeric resonances from monosaccharide residues are seen between 4.4 and 5.2 ppm. A group of three sharp signals between 5.0 and 5.2 ppm is attributable to α-anomeric protons, with signals between 4.4 and 4.8 ppm from β-anomers.

Fourier Transform Infra-Red Characterisation of PG Product

Freeze-dried samples of mucus glycoprotein are analysed by means of FTIR spectroscopy, using a Nicolet Magna-IR 860 spectrometer E.S.P. equipped with a liquid-nitrogen cooled mercury-cadmium-telluride (MCT) detector. Spectra are obtained by utilising a single-bounce ATR (attenuated-total reflection) zinc-selenide prism, over the range 680–4000 cm$^{-1}$.

Figure 2:
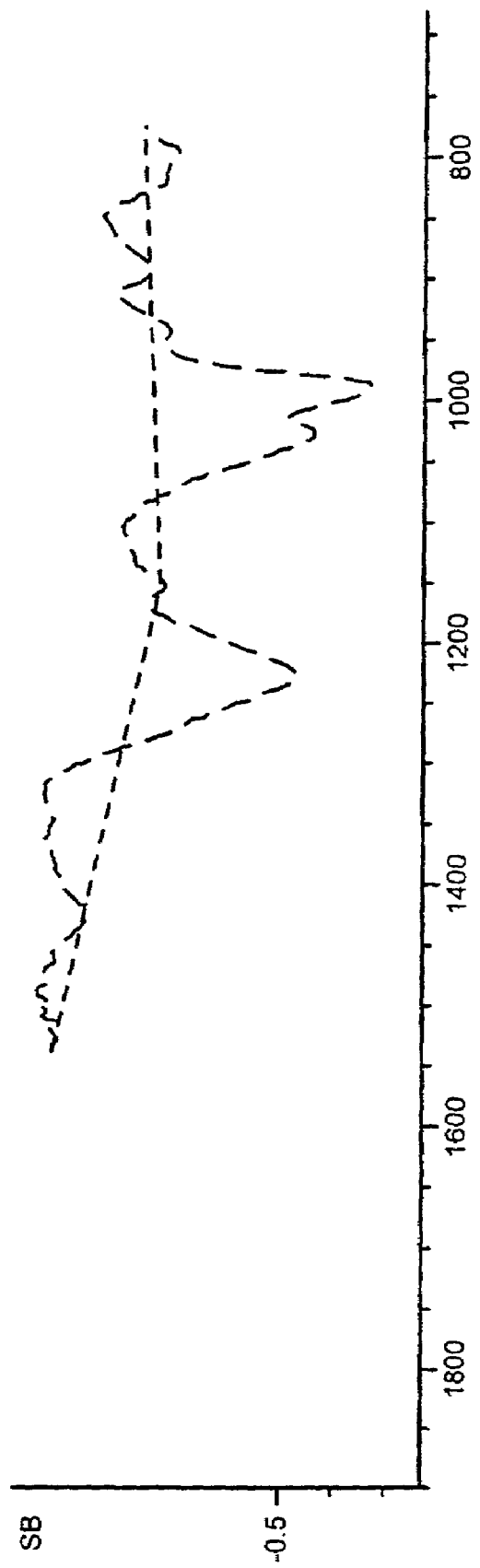
FIG. 2 shows FTIR spectra recorded from mucus glycoproteins.
Figure 3:
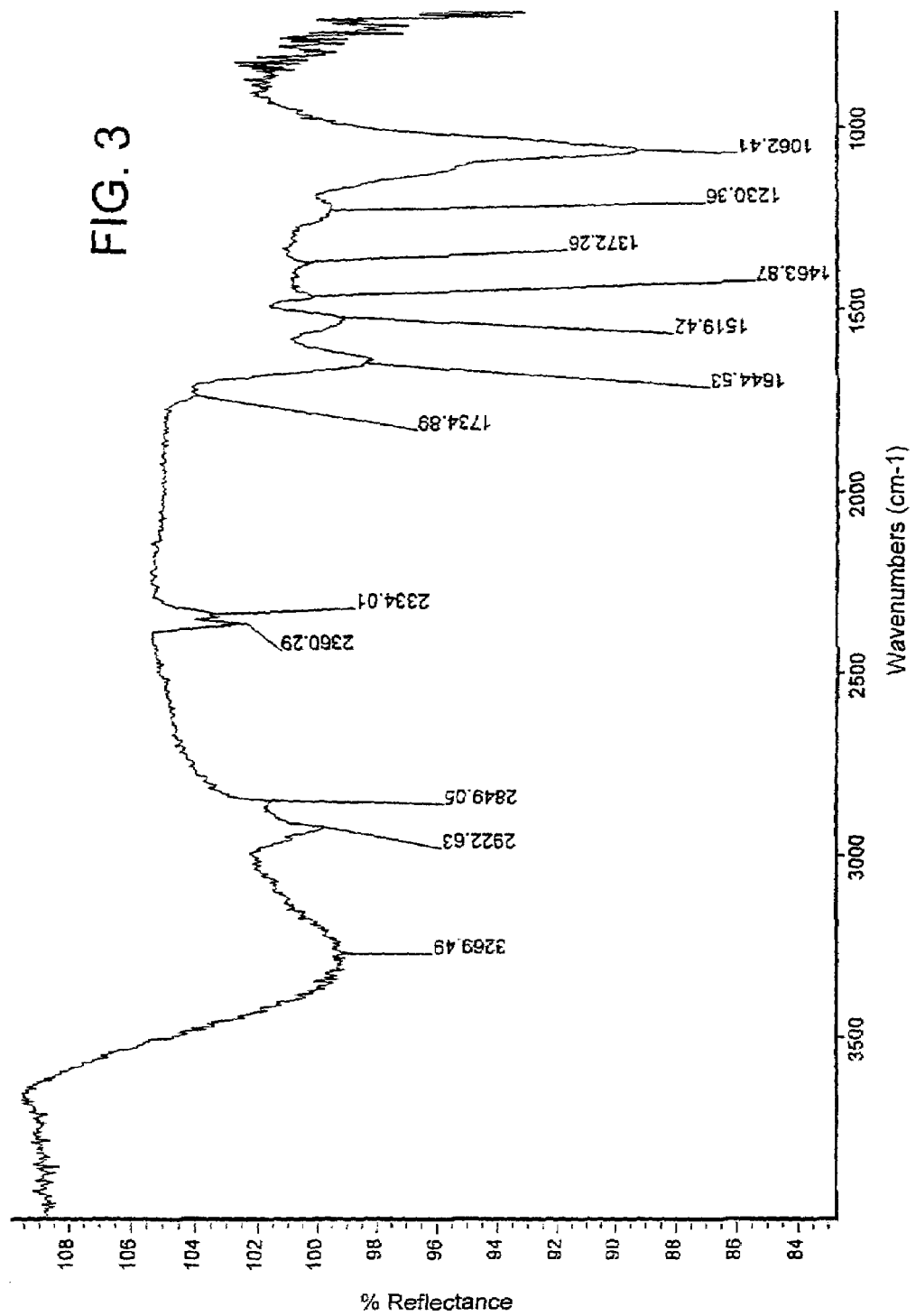
FIG. 3 shows FTIR spectra recorded from mucus glycoproteins, with annotated peaks.

FTIR spectra are recorded from mucus glycoproteins, and are shown in FIGS. 2 and 3, and peak assignment annotations are presented in table 2. The sulphate groups gave strong signals: SO$_2$-stretch 1335–1175 cm$^{-1}$, SO—R 1100–770 cm$^{-1}$, S=O stretch 1100 cm$^{-1}$. There are features at about 1650 cm$^{-1}$ which appear to arise form the N-acetyl group on the hexosamine sugar. There is a prominent feature at about 1050 which, in combination with the apparent abscence of a significant peak at about 1200, indicates that the *M. glacialis* glycoprotein is mainly 4-sulphated, without significant 6-sulphate and probably little, if any, N-sulphate.

The glycoproteins elute as a major peak, and one or more minor peaks, from a Q-Sepharose ion exchange column. The composition of *M. glacialis* glycoprotein indicates that it is relatively pure after size exclusion chromatography. The other products produce more complex chromatograms, indicating the presence of several species within the size-exclusion preparations.

The ion-exchange purified mucus glycoproteins from *M. glacialis* and *P. pulvillus* are resistant to digestion by proteinases K and papain. They are also resistant to neuramimidase and chondroitinases ACI and B, and heparinases, but a change in chromatographic profile indicates that they are sensitive to digestion by N-glycanase and chondroitinase ABC I. These results indicate that these glycoproteins are proteoglycans. Labelling with $^{35}$SO$_4$ suggests that the proteoglycan is sulphated.

TABLE 2

FTIR peak assignment information (see FIG. 3)

Vibrations Specific to Mucus proteoglycans

| | |
|---|---|
| 1062 | Sugar rings, many vibrations |
| 1230 | Sulphate, S=O stretch |
| 1372 | —OH bend |
| 1463 | CH$_2$ scissor |
| 1519 | N-acetyl group, N—H band |
| 1644 | N-acetyl group, C=O stretch |
| 1734 | Carbonyl group |

TABLE 2-continued

FTIR peak assignment information (see FIG. 3)

Vibrations not specific to proteoglycans

| | |
|---|---|
| 2334 | $CO_2$ |
| 2360 | $CO_2$ |
| 2849 | C—H |
| 2922 | C—H |
| 3269 | —OH |

Notes to Table 2:
Reproducible spectra may be obtained using different machines.
Spectra indicate that the disaccharide repeating unit of GAG chains is probably N-acetyl galactosamine-6-sulphate and glucuronic acid.

Analysis of Monosaccharides from *M. glacialis* Proteoglycan

Proteoglycan product from *M. glacialis* is subjected to methanolysis, and the resulting products are analysed by gas chromatography (GC).

Figure 4:
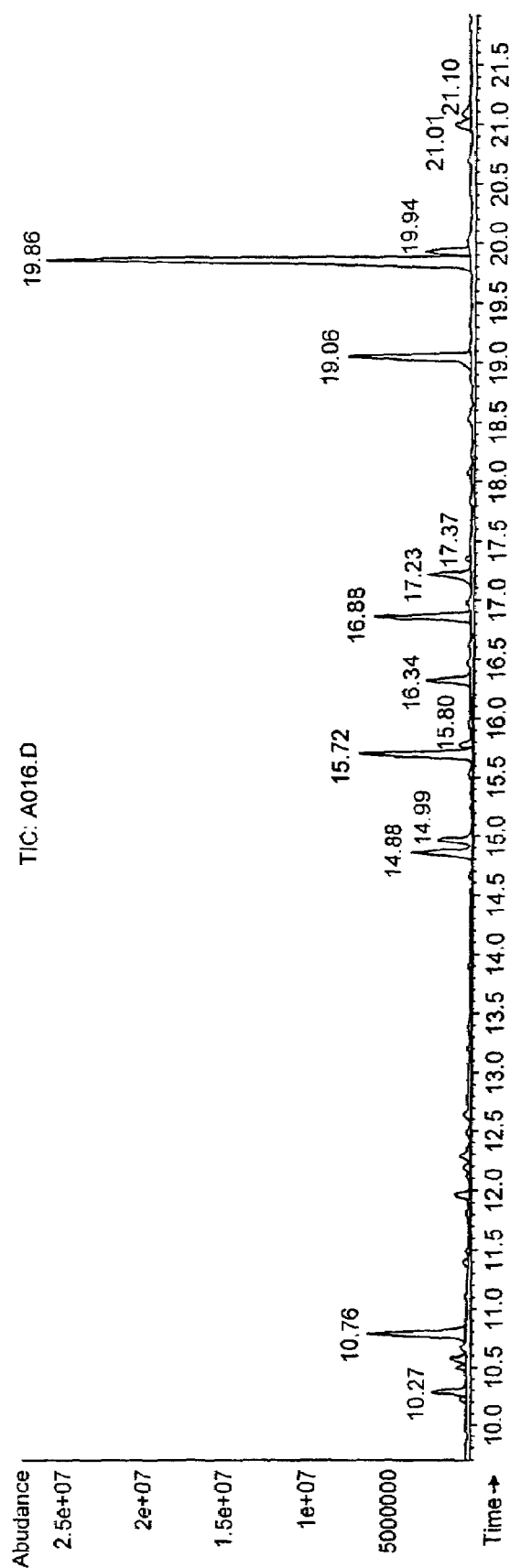
FIG. 4 shows a GC trace recorded from proteoglycan subjected to methanolysis, with annotated peaks.

GC data are presented in Table 3, and in FIG. 4 below.

TABLE 3

Gas Chromatography (GC) analysis of monosaccharides from *M. glacialis* proteoglycan after methanolysis.

| Retention Time | Monosaccharide |
|---|---|
| 10.27 | Unidentified pentose |
| 10.76 | Unidentified pentose |
| 14.88 | Mannose |
| 14.99 | Galactose |
| 15.72 | Galactose |
| 16.34 | Galactose |
| 16.88 | Glucose |
| 17.23 | Glucose |
| 21.01 | N-acetyl glucosamine |

Monosaccharide Composition of *M. glacialis* Product

Assays were performed by gas chromatography/mass spectrometry.

TABLE 4

Monosaccharides in samples of mucin from *M. glacialis*

| | Partially purified | | | | | |
|---|---|---|---|---|---|---|
| | nmoles | % of total | Pure Mg | % of total | Mg2 | % of total |
| Arabinose | 2.17 | 2.67 | 1.86 | 8.66 | 1.47 | 6.41 |
| Fucose | 3.03 | 3.72 | 0.36 | 1.68 | 0.74 | 3.22 |
| Xylose | 0.5 | 0.61 | 0.32 | 1.49 | 0.58 | 2.53 |
| Mannose | 2.09 | 2.57 | 1.67 | 7.77 | 1.64 | 7.15 |
| Galactose | 12.8 | 15.73 | 6.75 | 31.41 | 6.28 | 27.36 |
| Glucose | 5.76 | 7.08 | 3.71 | 17.26 | 4.38 | 19.08 |
| GalNAc | 30.75 | 37.78 | 2.7 | 12.56 | 3.45 | 15.03 |
| GlcNAc | 24.29 | 29.84 | 4.12 | 19.17 | 4.41 | 19.22 |
| Total | 81.39 | 100 | 21.49 | 100 | 22.95 | 100 |

For both the partially purified and pure samples over 70% of the material consists of glucose, galactose, N-acetyl galactosamine (GalNAc) and N-acetyl glucosamine (GlcNAc).

Purification reduces the proportion of GalNAc (by more than half) and also of GlcNAc, but increases the proportions of galactose and glucose present.

Minor components of the mixture are arabinose, mannose, fucose and xylose. The proportions of arabinose and mannose increase on purification, each to about 8% of the total in the purified preparation.

No uronic acids were found in any of these samples.

The monosaccharides tabulated above are similar to those found in coral mucin by Meikle et al. (1987) J. Biol. Chem. 262, 16941–47, but their proportions are substantially different. In the coral mucin, arabinose is the major component, making up nearly 50% of the sample; GlcNAc and mannose being the other two major sugars.

EXAMPLE 3

Antifoulant Properties (i) Inhibition of Bacterial Adhesion (Anti-Adhesive Properties)

Bacterial adhesion to cells such as bladder epithelial cells can be important in the inflammatory response. Inhibition of such adhesion may indicate anti-inflammatory properties.

Adhesion Assay with Vital Staining

In order to assess the anti-foulant/anti-adhesive properties of the mucus proteoglycans in regulating bacterial adhesion, a flow-chamber as described in (Usami et al., 1993: Biomed Eng vol 21 pp77–83) is used. The chamber is adapted in order to accommodate a removable microscope slide within a window in its base. A PTFE gasket separates the lid and base of the chamber. The assembly is designed to fit onto the stage of an inverted fluorescent microscope in order to carry out real time video microscopy studies.

*Pseudomonas fluorescens* (NCIMB, Pf 1079) cells are grown overnight at room temperature in Anderson's marine medium. Cultures are washed 3 times with filtered seawater (FSW) and then stained with the vital fluorescent dye SYTO9® (Molecular probes). Stained bacteria are diluted to 50 ml and incubated for 1 h in seawater alone or in seawater containing 1 mg/ml of mucus or control PG.

Fluorescent-labelled bacteria are pumped at a flow rate of 0.025 ml per second, which produces a linear range of shear of approximately 43–0 dyn. $cm^{-2}$. New glass microscope slides are fitted in the chamber for each experiment prior to pumping. Short sequences of the passage of bacteria through the chamber are recorded, in regions of low and high shear, by video microscopy. On completion of recording the chamber is flushed with filtered sea water and photographs are taken of adhered bacteria.

These studies indicate that mucus glycoproteins from *M. glacialis* but not from *P. pulvillus* or *O. nigra* are effective in inhibiting bacterial adhesion.

Adhesion Assay with Radioactive Labelling

In order to quantify the effect of mucus glycoproteins on bacterial adhesion a static assay is used to measure the adhesion of radiolabeled bacteria to model surfaces. *Pseudomonas fluorescens* are grown overnight at room temperature in Anderson's marine medium supplemented with 2.5 $\mu$Ci/ml $^3$H-methyl thymidine (Amersham Life Science Ltd., Amersham, U.K.). Cells from such cultures are pelleted by centrifugation at 250 g for 300s. Labelled bacteria are washed three times with filtered sea water (FSW) (0.2 $\mu$m filration) and re-suspended in FSW alone or FSW containing 0–1 mg/ml of mucus glycoprotein. They are then incubated for 3 h in 96-well tissue culture plates (Corning Costar Ltd., High Wycombe, U.K.). The suspension is discarded and plates are rinsed 3 times with FSW.

Adhered bacteria are lysed with 200 µl of 0.2 M NaOH, 1% SDS for 10 min and then neutralised with 200 µl of 0.2 M HCl. Radioactive label is quantified by scintillation counting after the addition of approx. 5 ml of Optiphase scintillation fluid (Zinnser Analytical Ltd., Maidenhead, U.K.).

Control PG and mucus glycoproteins are used to coat the wells of tissue culture plastic 96-well plates in order to measure the effect of immobilised PG on bacterial adhesion. Wells of 96-well plates are coated with poly-l-lysine (0.01%-1×10$^{-6}$%,) and glycoproteins (1×10$^{-5}$ ml at a concentration of 1 mg/ml) prior to adhesion assays. 200 µl of solution is incubated in each appropriate well for 1 hour after which the solution is discarded and the plates are dried at 60° C. for 1 hour. Adhesion of radiolabelled P. fluorescens is measured as described above.

Glycoproteins from P. pulvillus increase bacterial adhesion to tissue culture plastic in a dose-dependent manner. Mammalian heparin does not alter bacterial adhesion to tissue culture plastic. Dermatan sulphate increases bacterial adhesion to tissue culture plastic.

Studies of static adhesion using radiolabelled bacteria indicate that adhesion to tissue culture plastic is inhibited by 64%–68% by M. glacialis PG (34 µg/ml) but is enhanced by 131% by P. pulvillus PG. Adhesion is not significantly affected by glycoproteins from O. nigra. Heparin has no effect on adhesion. Dermatan sulphate (100 µg/ml) increases adhesion by 58%.

In order to measure adhesion of bacteria to the starfish cuticle, radiolabelled bacteria are incubated for 3 h with tube feet from M. glacialis. The tube feet are removed with scissors from a single specimen and rinsed with FSW. The contribution of surface groups to bacterial antifouling is assessed by digestion with specific enzymes. Tube feet are incubated with chondroitinase ABC, chondroitinase ACI, chondroitinase B or sulfatase enzymes. Controls are treated with digestion buffer only. Following digestion tube feet are rinsed with seawater, weighed and placed in wells of a 96-well plate. Radiolabeled bacteria (prepared as above) are than added and their adhesion is measured as described above. All treatments are performed in triplicate and adhesion results are normalised to the weight of each tube foot.

There is measurable adhesion of labelled bacteria to tube feet. This is increased by 20% by digesting tube feet with chondroitinase ABC. Treatment with chondroitinases ACI or B, or sulfatase, has no effect on bacterial adhesion. This indicates that a chondroitinase-sensitive surface PG contributes to the antifouling properties of the product. Chondriotinase ABC treatment reduces the anti-adhesive effect of the product.

Further studies of bacterial adhesion suggest that M. glacialis PG inhibits adhesion by causing bacteria to stick together in clumps These clumps are visible flowing through the chamber and settle in areas of low flow, but are washed away in areas of fast flow.

(ii) Inhibition of Adhesion Of Neutrophils to HUVECs

Adhesion of leukocytes or neutrophils to endothelial cells (such as vascular endothelial cells) can be an important event in the inflammatory response. Therefore, a product which inhibits this adhesion may posess anti-inflammatory properties.

Cellular Adhesion Assay.

In order to assess the effect of mucus proteoglycans (PGs) on cellular adhesion, an assay as described in (Kyan-Aung et al., 1991: J. Immunol. vol. 146, pp521–528) is used to measure the interaction between leukocytes and human vascular endothelial cells (HUVECs).

Polymorphonuclear leucocytes (>95% neutrophils) are isolated from citrated (not heparinised) human venous blood using Percoll gradients (density dependent centrifugation).

Cryo-preserved HUVECs (TCS Ltd. U.K.) are cultured in endothelial cell basal medium (MCDB 131) with appropriate supplements. Cells are passaged by trypsinisation and grown to confluency in the central wells of flat-bottomed 96-well plates. For adhesion assays, cells are used at the fifth passage.

Monolayers of HUVECs are stimulated for six hours with IL-1b (10 U/ml), LPS (2.5 mg/ml) or TNF-α(125 U/ml) in the absence and presence of mucus glycoproteins diluted in saline, or heparin and poly-glutamic acid controls. Following stimulation, monolayers are washed to remove stimuli and inhibitors, before the addition of 2×10$^5$ radiolabelled leukocytes to each well. Following a 30 minute incubation at 37° C. non-adherent cells are removed by gentle aspiration and washing. The adherent cells in each well are lysed with 1% Nonidet-P40, placed in scintillation vials and counted on a γ-counter.

The adhesion of leukocytes stimulated with the peptide fMLP to unstimulated HUVECs is also measured. Plates are incubated for a further 30 minutes at 37° C., and are then treated as described above.

Initial cell adhesion studies are carried out with unpurified samples of mucus glycoprotein from M. glacialis. These proved to be highly cytotoxic, causing cell lysis within 5 minutes. Partially purified mucus glycoproteins are found not to be cytotoxic, and inhibit neutrophil adhesion in a dose dependent manner (0.0001–1 mg/ml range).

Adhesion of leukocytes to endothelial cells is inhibited by proteoglycans (PGs) from M. glacialis.

Adhesion of radiolabelled human leukocytes to endothelial cells is inhibited by 68% by proteoglycans from M. glacialis.

EXAMPLE 4

Raising Of Antibodies Against Product

Raising of Polyclonal Antibodies Against Proteoglycan (PG) Product

Three aliquots of 150 µg, 250 µg and 250 µg of purified proteoglycan (PG) antigen are emulsified with equal volumes of Freuds adjuvant and injected intramuscularly into a rabbit over a period of three weeks at intervals of 1, 7 and 21 days. Blood was collected two weeks after the final injection and incubated at room temperature for 1 h and at 4° C. overnight to allow for clotting. The serum is centrifuged twice at 5000 g for 10 min before an equal volume of glycerol is added to the serum. Sodium azide is added to a final concentration of 0.02% (w/v). This antiserum is stored at −20° C.

EXAMPLE 5

Lack of Anticoagulant Effect Compared to Heparin

M. glacialis PG produced according to the invention does not have a significant anti-coagulant effect when compared with heparin in a coagulation assay.

Inhibition of coagulation or clotting (ie anti-coagulant properties) are estimated by measuring the activated partial thromboplastin time (APTT) according to Thompson and Harker 1983 (Manual of Hemostasis and Thrombosis Davis Company, Philadelphia).

| Treatment | APTT clotting time (n = 5) |
| --- | --- |
| control clotting time | 39.2 ± 1.4 s |
| 0.1 mg per ml mucus PG | 39.9 ± 1.6 s |
| 0.1 µg per ml mucus PG | 39.1 ± 1.5 s |
| 50 heparin units per ml | >600 s |
| 0.05 heparin units per ml | 43.8 s |

Thus, proteoglycan perparations according to the invention have potent anti-adhesive properties in both mammalian cell and bacterial cell adhesion (see above) without anticoagulant activity.

EXAMPLE 6

Anti-Adhesive Effects OF Product

The effects on neutrophil-endothelial adhesion are monitored. f-met-leu-phe stimulated neutrophil adhesion to unstimulated HUVECs is assayed using neutrophils from three separate donors. Assays are carried out in triplicate.

Inhibition of cellular adhesion is observed. Representative results are found in FIG. 5.

Unstimulated neutrophil adhesion to IL-1β stimulated HUVECs is assayed. Assays are carried out in triplicate. Inhibition of cellular adhesion is observed.

The anti-adhesive properties of the product according to the invention are clearly demonstrated.

EXAMPLE 7

Preparation and Use of Product

Introduction

Biofouling describes the unwanted coating of surfaces by organic molecules and organisms[1] Marine invertebrates have developed effective mechanisms for preventing biofouling[2] which may include the generation of a non-stick surface.

The product as described herein modulates the adhesion of inflammatory cells to the human vascular endothelium.

Fourier transform infrared spectropscopy (FTIR) of the cuticular surface of the starfish *Marthasterias Glacialis* and of the surface of cultured human vascular endothelial cells (HUVECs) demonstrated the presence of sulphated molecules. Bacterial adhesion to the starfish surface was enhanced by enzymatic removal of these molecules which, in a partially purified form prepared as disclosed herein, are found to inhibit bacterial adhesion to plastic. Furthermore, the adhesion of human leucocvtes to vascular endothelium is inhibited by the product, demonstrating its anti-adhesive function, and modulation of cellular adhesion.

In mammalian systems, the vascular endothelium is in constant, direct contact with the blood, providing a barrier between circulating blood elements and underlying tissue structures. This monolayer of cells is involved in regulation of the passage of cells from the blood into tissue sites, during host-defence and inflammation, via production of specific surface molecules which direct the adhesion of blood cells expressing relevant counterligands.[3] Under normal circumstances, the endothelium does not promote the adhesion of other cells to itself, ie. it has anti-adhesive properties.

The glycosaminoglycan (GAG) heparin, which is released from mast cells during inflammation, has long been known to modulate cell recruitment and other aspects of the inflammatory response in mammals[7,8] and has direct inhibitory effects upon adhesive interactions between endothelial and inflammatory cells.[9,10,11,12] It should be noted that heparin, being more heavily sulphated than heparan sulphate and thus possessing a higher net negative charge, has greater anti-inflammatory effects than heparan sulphate, [13,14] when either substance is added exogenously to a mammalian system, suggesting that endogenous heparin may act to augment the anti-adhesive properties of the endothelium, possibly through replacement of heparan sulphate molecules.[15] The anti-adhesive role of GAGs is not confined to cells of the vascular system in that epithelial surfaces are also known to present a layer of these molecules to their environment. For example, the epithelium of the urinary bladder is able to resist bacterial and macromolecular interactions in this manner and disruption of the GAG layer is associated with epithelial leakiness and bacterial infection.[16,17] Interstitial cystitis, a condition characterised by such leakiness, can be treated successfully with exogenous GAGs and other polysulphated molecules, such as pentosan polysulphate,[18] when administered by direct instillation to the bladder or via the oral route.

Lower organisms, such as bacteria, are thought to utilise polysaccharide-rich glycocalyces for a range of biological functions, including cell recognition,[19] but which also have anti-adhesive roles.[20] Of particular interest is the echinoderm class of marine invertebrates, which are able to maintain a surface relatively free of biofilms and bacterial colonisation,[21] despite being continually exposed to sea water containing many fouling organisms. Maintenance of a biofilm-free surface is important for normal function(s) of these organisms, such as feeding, gaseous exchange and motility. This property is dependent upon the integrity of a cuticular epidermis, the surface of which is rich in complex glycoproteins.[22] Areas of the echinoderm surface which show loss of this cuticle can exhibit bacterial colonisation, providing a parallel to the effects of disruption of epithelial or endothelial GAGs with regard to cellular adhesion in mammalian systems.

As disclosed herein, we have examined the mechanisms by which echinoderms prevent biofouling of their surfaces and have related these mechanisms to a mammalian model of cellular adhesion. Through use of attenuated total internal reflection FTIR we have been able to examine the intact surface of the echinoderm *Marthasterias Glacialis*. Without the need for fixing of sample, a process which can lead to loss of the outermost layers.[24] Spectra of untreated, wet tube feet from *M. Glacialis* are compared to those obtained from tube feet treated with sulphatase type VII enzyme. The changes in spectra resulting from enzymatic treatment suggest the presence of sulphated molecules on the surface of the epidermis, in that peaks which indicate the presence of sulphur-containing functional groups were absent on spectra from enzymatically digested samples when compared to those obtained from untreated controls. This disclosure adds to previous biochemical observations that chondroitinase-sensitive GAGs are present in the echinoderm cuticle,[25] as our data localise these molecules to the actual surface of the sample. By way of comparison, living HUVECs were examined using the same FTIR method, which has not previously been accomplished.

Differences in sulphation patterns were observed in the spectra of untreated endothelial cells when compared to those from enzymatically (heparinase) modified cells.

Interestingly, addition of exogenous heparin to enzymatically treated HUVECs led to restoration of the sulphate peak in the spectra of these cells, with introduction of additional peaks, found in the spectrum of heparin itself, suggesting a 'replacement' of endothelial heparan sulphate by heparin. Taken as a whole, these results demonstrate the presence of sulphated molecules on the surfaces of viable cells from both human and marine invertebrate tissues and, without wishing to be bound by theory, may provide a possible mechanistic explanation for the properties of the product according to the invention.

Given the pathophysiological consequences of GAG disruption in human disease, the product of the invention may be useful therein.

Cellular Adhesion

The effects of artificial removal of *M. Glacialis* cuticular GAGs upon bacterial adhesion to these surfaces are investigated. It is found that chondroitinase ABC digestion of tube feet leads to an increase in the adhesion of radiolabelled *Pseudomonas flourescens* to these structures.

The anti-adhesive properties of mucus from *M. Glacialis* were investigated using in vitro adhesion assays. Adhesion of radiolabelled bacteria to tissue culture plastic is strongly inhibited by a solution of the mucus product which had been purified by chromatography, demonstrating an anti-adhesive role for the product in vivo.

In order to demonstrate whether the anti-adhesive actions of the product are transferable to a mammalian system, its effects are assessed in an in vitro model of endothelial-leucocyte adhesion.

The compound, purified as described herein, is found to inhibit the adhesion of radiolabelled human neutrophils to cultured human umbilical vein endothelial cell monolayers. This inhibition occurs in a concentration dependent manner. This inhibition occurs under different conditions of cellular activation, ie when neutrophils are stimulated with the chemotactic peptide fMLP, and when HUVECs are stimulated with the cytokine IL-1β. The inhibitory effects of the product are greater than those of unfractionated heparin, when applied to the same system. Furthermore, the product is found to lack the anticoagulant actions of heparin, as measured by activated partial thromboplastin time and also lacks cytotoxic activity.

Methods for Example 7

FTIR Analysis of the Echinoderm Surface

Tubefeet were removed from the starfish Marthasterias glacialis immediately prior to analysis. Samples were placed directly onto a zinc-selenide FTIR crystal and excess water removed by blotting. ATR-FTIR spectra were taken using a 6021 Galaxy Series spectrometer (Mattson Instruments Ltd., U.K.), set at 50 scans per run. In some experiments, the tissue samples were treated with the enzyme sulphatase type VIII (Sigma-Aldrich Company Ltd., Poole, U.K.; 15 minutes incubation at 37° C., 50 Uml$^{-1}$ in 0.4M Tris-HCl buffer, pH 7.9) prior to analysis as above.

FTIR Analysis of the Endothelial Surface

HUVECs (TCS Ltd., Milton Keynes, U.K.) were cultured to confluency in 6-well tissue culture plates (Corning Costar Ltd., High Wycombe, U.K.) at 37° C./5% $CO_2$, in medium (MCDB 131) supplemented with foetal bovine serum (2%), hydrocortisone (1 ng ml$^{-1}$), gentamicin (50 μg ml$^{-1}$), amphotericin-B (50 ng ml$^{-1}$) and human epidermal growth factor (10 ng ml$^{-1}$).

Cultures were washed three times with phosphate buffered saline, to remove culture medium, and some wells were incubated with heparinase I, II, III or a combination of these enzymes (Sigma-Aldrich; 60 minutes at room temperature).

Following heparinase treatment, monolayers were washed and some of these wells subsequently received unfractionated heparin (5000 U ml$^{-1}$ Multiparin®, CP Pharmaceuticals Ltd., Wrexham, U.K.; 20 minutes at room temperature) and were washed again. Cells were scraped from the plates using a rubber policeman, blotted onto the FTIR crystal and gently dried under nitrogen to remove excess buffer. 60 second scans of the cells were made (as before). In addition, the spectrum of unfractionated heparin was taken.

Preparation of Mucus Extract

Mucus was collected from the starfish Marthasterias glacialis using a fine glass pipette under suction. Particulate matter was eliminated by centrifugation and the supernatant applied to a Sepharose CL-6B column (950 mm×26 mm diameter). Polysulphated molecules eluted in the void volume were collected and dialysed against distilled water before freeze drying.

Bacterial adhesion assay

*Pseudomonas flourescens* organisms (NCIMB, Pf 1079) were cultured overnight at room temperature in Anderson's marine medium (prepared in-house) supplemented with 0.09 MBq ml$^{-1}$ $^3$H-methyl thymidine (Amersham Life Science Ltd., Amersham U.K.). Cultures were pelleted by centrifugation (5 min, 250 g) and washed with 0.2 μm-filtered sea water (FSW). Radiolabelled bacteria were resuspended in FSW and incubated for 3 h at room temperature in 96-well tissue culture plates (Corning Costar), some of which had been coated with partially purified starfish mucus extract (200 μl of solution incubated in wells for one hour removed and plates dried at 60° C. for one hour).

Non-adherent bacteria were removed by washing with FSW and adherent bacteria lysed (0.2M NaOH, 1% sodium dodecyl sulphate). Radioactivity in lysates was measured by scintillation counting, following the addition of 5 ml scintillation fluid per sample (Optiphase®. Zinnser Analytical Ltd., Maidenhead. U.K.)

Leucocyte-endothelial Adhesion Assay

HUVECs (TCS) were cultured to confluency, as before, in flat-bottomed 96-well tissue culture plates for use in adhesion assays described previously.[12] Briefly, some wells were stimulated with 10 U ml$^{-1}$ human recombinant interleukin 1β (Sigma), in the absence and presence of unfractionated heparin (Multiparin®) or partially purified mucus extract. Neutrophils were isolated from the venous blood of healthy volunteers by density-dependent centrifugation on discontinuous Percoll gradients (55% on 70% on 81%, 1750×g, 25 minutes), following removal of erythrocytes by sedimentation on an equal volume of 6% dextran solution (40 minutes, room temperature). Neutrophils were radiolabelled with $^{51}$Cr for one hour at room temperature (aqueous sodium chromate, 37 MBq ml$^{-1}$, Amersham), washed and applied to HUVEC monolayers. 2×10$^5$ cells in Hank's balanced salts solution (Sigma) were added to each well of HUVECs and incubated for 5 minutes, following which, some wells were stimulated by addition of 10$^{-6}$M fMLP (Sigma) as a neutrophil activator. Plates were incubated at 37° C. for a further 25 minutes. At the end of this period, wells were washed to remove non-adherent cells and adherent cells lysed with 1% Nonidet P40 (Sigma). Radioactivity in lysates was quantified by gamma-counting.

Effect of Product Upon Bacterial Adhesion

Adhesion of radiolabelled *Pseudomonas flourescens* to tube feet from Marthasterias glacialis was increased significantly (*P<0.05) following enzymatic digestion of the cuticular surface with chondroitinase ABC.

Partially purified mucus extract from the surface of *M. glacialis* inhibited significantly (*P<0.05) the adhesion of radiolabelled *P. flourescens* to tissue culture plastic.

Effect of Product Upon Leucocyte Adhesion to Human Umbilical Vein Endothelial Cells (HUVECs)

Adhesion of radiolabelled human neutrophils to IL-1β-stimulated HUVECs is inhibited significantly (*P<0.05) in the presence of either unfractionated heparin (porcine origin, Multiparin®, CP Pharmaceuticals), or partially purified starfish mucus extract product.

Adhesion of fMLP-stimulated radiolabelled human neutrophils to HUVECs is also inhibited significantly (*P<0.05) by either unfractionated heparin or the starfish product.

EXAMPLE 8

Properties of the Product of the Invention

Mucus is collected from the starfish *Marthasterias glacialis* and *Porania pulvillus*, and the brittlestar *Ophiocomina nigra*, and fractionated by size exclusion chromatography. A high molecular weight, glycoprotein-rich fraction is collected from each species. These preparations are sufficiently pure to perform functional studies and compositional analyses.

NMR studies indicate that the preparations contain complex polysaccharides with spectra unlike previously characterised glycoproteins. Fourier-transform infrared (FTIR) spectra of the mucus glycoproteins share many characteristics with spectra from mammalian mucins. Monosaccharide analysis of the product demonstrates a composition consistent with a mucin-type glycoprotein.

The purified mucin products from *M. glacialis* and *O. nigra* inhibit in vitro bacterial adhesion in a dose dependent manner. In contrast, the purified mucin product from *P. pulvillus* promotes bacterial adhesion in a dose-dependent manner. All of the mucin products inhibit the adhesion of human neutrophils to cultured human vascular endothelial cells (HUVECs), and have no detectable anticoagulant activity. The mucus products described here have adhesion regulating functions that may have a role in the antifouling. These mucin products will clearly be of therapeutic value, such as through their ability to regulate human neutrophil adhesion.

Proteoglycans

Proteoglycans (PGs) are glycoproteins, characterised as a core protein with one or more covalently attached glycosaminoglycan (GAG) chains[8] The core protein may also bear varying amounts of covalently attached N— and O— linked oligsaccharides[9]. The GAGs have a linear repeating disaccharide structure of a hexosamine residue and a uronic acid residue, up to approximately 100 residues[9]. These sugar residues can be —N— or —O— sulphated in a number of positions and combination of sulphate and carboxylate groups means that PG are highly negatively charged and hydrophilic[8]. Proteoglycans are present on all mammalian cell surfaces where they can regulate cell-matrix, cell-cell, and cell ligand interactions[10].

This Example is directed at establishing the identity and/or antifouling properties of glycoproteins in mucus products according to the invention.

Fouling of the surface of living organisms may be life threatening because it can impair vital surface processes, such as gas exchange.

Glycoprotein products are purified from the mucus of a predatory starfish and are compared to similar glycoproteins purified from a filter feeder starfish and a brittlestar. The structures of PGs extracted from sea cucumbers [13-15] have previously been reported, and there has been a single study mucus glycoproteins from the coral *Acropora formosa*[16].

Disclosed herein are compositions of novel glycoprotein products, as well as their characteristics, and methods for their preparation.

Experimental Procedures of Example 8

Materials

All chemicals were obtained from Sigma (Poole, Dorset, UK), unless otherwise stated. All plasticware was from Corning (High Wycombe, Bucks, UK), unless otherwise stated.

Animals and collection of mucus

Divers collected specimens of the starfish *Marthasterias glacialis* from sea lochs on the West Coast of Scotland. Trawling was used to collect specimens of the brittlestar *Ophiocomina nigra* and the cushion star *Porania pulvillus*. Specimens were transported in fresh seawater and transferred to aerated through-flow sea water aquaria. Starfish were kept at a density of 30 animals per 500 liter tank. *M. glacialis* were fed mussels (*Mytilus edulis*) collected locally. *P. pulvillus* and *O. nigra* were able to obtain sufficient food from the seawater supply.

Mucus was collected from *O. nigra* and *M. glacialis* in response to physical stress. Specimens were placed in a large glass funnel and agitated with a glass rod. After a few minutes large amounts of mucus was secreted in response to this stress. The mucus was collected in 50 ml centrifuge tubes.

Mucus was also collected from *M. glacialis* and *P. pulvillus* using suction. The mucus was aspirated from the dorsal surface of both species using a fine glass Pasteur pipette connected to a reservoir under suction. Animals were first blotted with paper towel to remove excess seawater. *M. glacialis* and were kept for periods up to 12 months and appeared to be unharmed by weekly mucus collection. *P. pulvillus* developed surface lesions after several weeks of mucus collection, possibly due to cuticular damage associated with mucus collection.

Mucus was stored at 4° C. prior to processing.

Purification of glycoprotein products from mucus

Mucus samples were clarified by centrifugation at 500 g for 10 min. Five ml of supernatant were applied to a column of Sepharose CL-6B (100 cm×2.6 cm, Pharmacia Biotech) which had previously been equilibrated with 0.9% NaCl solution. The sample was eluted at a flow rate of 2.5 ml. $min^{-1}$ with 0.9% NaCl. The eluant from the column passed through a Spectromonitor 4100 absorbance detector (LDC) and its absorbance at 280 nm monitored continually using Thermochrom II software. Fractions were collected every 3 minutes in 10 ml glass test-tubes using a Pharmacia LKB Frac-100 fraction collector. Protein and sulphated-glycan content of fractions was assayed as described below. The column was calibrated with a gel filtration high molecular weight calibration kit (Pharmacia Biotech) in accordance with the manufacturer's instructions.

Glycan product is eluted in the void volume of the Sepharose CL-6B column. These fractions were pooled and dialysed (MW cut off 12,000; Philip Harris Scientific) against distilled water. The dialysed samples were then either freeze-dried or further purified by application to a column packed with Q-Sepharose high performance (10 cm×1.6 cm. Pharmacia Biotech) equilibrated with 0.01 M Tris HCl buffer, pH 8.0. Two hundred μl of samples of mucus PG were loaded at one time and eluted with a rising concentration of NaCl (0–1 M over 10 minutes) in 0.01 M Tris HCl, pH 8.0. The absorbance of the eluant at 280 nm was monitored and 1 ml fractions were collected as described before.

The purified glycoproteins are dialysed against three changes of a hundred volumes of distilled water over 24 h, and freeze dried for long term storage at −20° C.

Mucus glycoproteins were treated with the enzymes papain, chondroitinases ACI (Grampian enzymes), B (Grampian enzymes), and ABC (Sigma). The digests were analysed by ion-exchange chromatography using the Q-sepharose high performance column as described.

Protein and Glycan Assays

The protein content of fractions collected from columns was measured using Coomassie® Plus reagent (Pierce). Albumin standards were prepared in the range 0–25 $\mu$g. ml$^{-1}$. The absorbance of standards and samples at 595 mm was measured in 96-well plates using a Biotek EL 340 plate reader. Standard curves and concentrations of unknowns were calculated using Kineticalc II software.

The concentration of sulphated-polysaccharides in fractions collected from columns was estimated using the dimethylmethylene blue assay, which has traditionally been used as an assay for glycosaminoglycans[17] but which detects other sulphated polysaccharides. Heparin (Multiparin™, CP pharmaceuticals), chondroitin sulphate C (Shark cartilage, Sigma), and bovine mucin (Type 1S, Sigma) were all used, equally effectively, to produce standard curves in the range 0–10 $\mu$g. ml$^1$. The absorbance of standards and samples at 490 nm was measured in 96-well plates using a Biotek EL 340 plate reader. Standard curves and concentrations of unknowns were calculated using Kineticalc II software.

The uronic acid content of samples was determined after acid hydrolysis (6.0 M HCL at 100° C. for 6 h) by the modified carbazole reaction[18], and the hexosamine content was determined by the Elson-Morgan reaction[19]. Standard curves for hexosamine and hexuronic acid were constructed from glucosamine and glucuronic acid.

SDS-PAGE of Mucus Glycoproteins

The purity and molecular weight of glycoprotein samples were estimated using SDS-PAGE. Freeze-dried samples were reconstituted in sample buffer (0.1 M phosphate buffer pH 7.0, 1% w/v SDS, 1% v/v 2-mercaptoethanol, 0.15 g. 1$^{-1}$, 6 M Urea) at a concentration of 1 mg. ml$^{-1}$ and heated at 60° C. for 3 h. High molecular weight standards (97.4 Kda –584.4 Kda, Sigma) were prepared in accordance with manufacturers instructions. Fifteen microlitres of sample was applied to each well of a 3.5% reducing polyacrylamide get (20 cm×20 cm) with 7% polyacrylamide gel for the well walls. The samples were separated overnight at 30 mA. Gels were fixed overnight in a methanol, acetic acid and distilled water (10:35:55) on an orbital shaker. Gels were then stained by the periodic acid—Schiff's reagent method and destained in several changes of fixative overnight. The relative mobility of the standards was used to estimate the molecular weight of samples.

Monosaccharide Analysis of Mucus Glycoproteins

The monosaccharide composition of purified and partially purified mucus glycoprotein was determined by gas chromatography mass spectrometry (GC-MS) after methanolysis. Acid methanolysis of samples and standards was performed using 0.5 M HCl in dry methanol., according to the method of Ferguson[20]. The trimethylsilyl ethers of the neutral and amino sugars were determined by GC-MS using a column according to the method of Ferguson[20]. Uronic acids were determined in a separate experiment by the method of Inoue and Miyawaki[21]. Briefly; samples were methanolysed in 1.0 M methanolic HCl at 100° C. overnight, dried and analysed as their trimethylsilyl ethers by GC/MS.

NMR Characterisation of Mucus Glycoproteins

Samples were dissolved in 99.8% $D_2O$ and transferred to 5 mm NMR tubes. Proton and carbon NMR spectra were recorded using a Varian Unity 500 NMR spectrometer, at temperatures of 45° C. or 70° C.

FTIR characterisation of mucus PG

Mucus samples, mammalian PGs and mammalian mucins were analysed by means of FTIR spectroscopy, using a Nicolet Magna-IR 860 spectrometer E.S.P. equipped with a liquid-nitrogen cooled mercury-cadmium-telluride (MCT) detector and an Inspect Plus IR microscope attachment. Spectra were obtained by utilizing a single-bounce ATR (attenuated-total reflection) zinc-selenide prism, and by transmission through KBr tablets, over the range 680–4000 cm$^{-1}$. For each spectrum 32 scans were co-added at a spectral resolution of 4 cm$^{-1}$.

Real-Time Adhesion Assay

In order to demonstrate the utility of mucus glycoprotein products in regulating bacterial adhesion, a flow-chamber was built to carry out real time video microscopy studies under flow.

A linear shear stress flow chamber was constructed using the design of Usami et al[22] with minor modifications. The chamber was adapted in order to accommodate a removable microscope slide within a window in its base. A PTFE gasket separated the lid and base of the chamber, which were secured by 8 screws. The thickness of the gasket determined the width of the gap within the flow chamber. A variety of blank gaskets were provided within which windows could be cut with a scalpel and template. The assembly was designed in order to fit on the stage of an inverted fluorescent microscope (Zeiss, Axiovert) and allow access to the whole area of the flow chamber. *Pseudomonas fluorescens* (National Collection of Industrial Marine Bacteria Ltd., Pf 1079) were grown overnight at room temperature in Anderson's marine medium. Cultures were pelleted by centrifugation (5 min. 250 g) and washed 3 times with filtered (0.22 $\mu$m) seawater. The washed bacteria were then re-suspended in 5 ml of filtered seawater and stained with 5 $\mu$l of the vital fluorescent dye SYTO® 9 (Molecular probes) for 10 minutes. The bacteria were then diluted to 50 ml and incubated for 1 h in seawater alone or in seawater containing 1 mg. ml$^{-1}$ of mucus or control PG. Following this incubation bacteria were transferred to the flow chamber.

Fluorescent-labelled bacteria were pumped into a sealed reservoir flask using a peristaltic pump. The speed of the pump was adjusted to give a flow rate of 0.025 ml seconds' in order to produced a linear range of shear of approximately 43–0 dyn. cm$^{-2\,22}$ New glass microscope slides (Gold Star washed, Phillip Harris) were fitted in the chamber for each experiment prior to pumping. The passage of bacteria through the chamber was recorded using a video camera (JAC, TK-C1381) mounted on the microscope. Short sequences were recorded in regions of low and high shear. On completion of recording the chamber was flushed with filtered seawater for 5 min, and stills photographs of the remaining adhered bacteria were taken.

Bacterial adhesion assay

The effect of mucus glycoprotein products on the adhesion of radiolabeled bacterial was measured in vitro.

*Pseudomonas fluorescens* (NCIMB, Pf 1079) were grown overnight at room temperature in Anderson's marine medium supplemented with 2.5 $\mu$Ci. ml$^{-1}$ $^3$H-methyl thymidine (Amersham). Cultures were pelleted by centrifugation (5 min, 250 g) and washed 3 times with filtered (0.2 $\mu$m) seawater. Labelled bacteria were resuspended in FSW and incubated for 3 h at room temperature with 96-well tissue culture plates (Corning Costar). Bacteria were then discarded and the plates were washed 3 times with FSW. Adhered bacteria were solubilised with 200 $\mu$l of 0.2 M NaOH, 1% SDS for 10 min and then neutralised with 200 $\mu$l of 0.2 M HCl. Radioactivity was quantified by scintillation counting following the addition of ~5 ml of Optiphase scintillation fluid (Zinnser Analytical Ltd.).

The adhesion of *P. fluorescens* in response to a range of concentrations of soluble mucus and control PGs was measured on tissue culture plastic as described. The same samples were also used to coat the wells of tissue-culture plastic 96-well plates in order to measure the effect of adsorbed samples on the adhesion of *P. fluorescens*. Wells of 96-well plates were coated in triplicate with mucus glycoproteins (1 mg ml-1)poly-1-lysine (0.01–1×10$^{-6}$%,) and proteoglycans (1 mg. ml$^{-1}$–1×10$^{-5}$ ml) prior to adhesion assays. Briefly 200 $\mu$l of solution was incubated in each well for 1 h after which the solution was discarded and the plates were air dried at 60° C. for 1 h.

Cellular adhesion assay

In order to assess the effect of mucus glycoproteins on cellular adhesion an assay that measures the interaction between leukocytes and human vascular endothelial cells (HUVECs) was used.

The adhesion assay used is based upon a method described by Kyan-Aung et al.[23]. In brief, cryopreserved HUVECs (TCS Ltd. U.K.) were cultured in endothelial cell basal medium (MCDB 131) supplemented with foetal bovine serum (2%), hydrocortisone (1 ng ml$^{-1}$), gentamicin (50 $\mu$g ml$^{-1}$), amphotericin-B (50 ng ml$^{-1}$) and human epidermal growth factor (10 $\mu$g ml$^{-1}$). Cells were passaged by trypsinisation (0.025% trypsin with 0.01% EDTA) and were grown to confluency in the central wells of flat-bottomed 96-well plates in a volume of 200 $\mu$l of culture medium per well. For adhesion assays, cells were used at the fifth passage.

Monolayers of HUVECs were stimulated for six hours with IL-1b (10 Uml$^{-1}$) LPS (2.5 mg ml$^{-1}$) or TNF-$\alpha$ (125 U ml$^{-1}$) in the absence and presence of mucus PGs diluted in normal saline, or heparin (Multiparin) and poly-glutamic acid controls. Following stimulation, monolayers were washed to remove stimuli and inhibitors, before the addition of 200 $\mu$l radiolabelled leukocytes suspension to each well (2×10$^5$ cells per well). Following a 30 minute incubation at 37° C. non-adherent cells were removed by gentle aspiration and washing. The adherent cells in each well were lysed with 1% Nonidet-P40, placed in scintillation vials and counted on a g-counter.

The adhesion of leukocytes stimulated with the peptide fMLP to unstimulated HUVECs was also measured. Plates were incubated for a further 30 minutes at 37° C. and were then treated as described before.

Mucus collected by aspiration is a viscous acidic liquid. Stress mucus was less viscous and of lower pH.

Whole mucus samples from *M. glacialis, O. nigra*, and *P. pulvillus* were fractionated by size exclusion chromatography. In every case the major sulphated-polysaccharide containing peak eluted in the void volume, indicating the presence of a high molecular weight glycoconjugate. The fractions from this peak were pooled and dialysed for further purification or freeze-drying. The freeze-dried fraction is referred to as the 'partially purified' glycoprotein and was used in all functional assays.

Fifty milliliters of mucus from *M. glacialis* yielded approximately 50 mg of partially purified glycoprotein. This migrated as a one high molecular weight band, which hardly entered the gel, and two low molecular weight bands (Mr 240 kDa and 177 kDa) on a polyacrylamide gel.

Fifty milliliters of *O. nigra* mucus yielded approximately 5 mg of freeze-dried sample, which migrated as single band indicating a molecular weight of approximately 490 kDa.

Twenty milliliters of *P. pulvillus* mucus yielded approximately 3 mg of freeze-dried sample, which migrated as a two high molecular weight bands (Mr 787 kDa and 669 kDa) and one low molecular weight band (Mr 28 kDa) on a polyacrylamide gel.

Properties of Mucus Glycoproteins

The partially purified glycoprotein product from *M. glacialis* was susceptible to digestion by papain and pronase. Digestion by chondroitinases was negligible.

Analysis by the carbazole reaction and the modified Elson-Morgan reaction indicated that mucus glycoproteins from *M. glacialis* and *P. pulvillus* contained both hexuronic acid and hexosamine. As no uronic acids were detected by GC-MS it is likely that neutral and amine sugars, which are known to interfere with the carbazole reaction, were responsible for the levels detected.

Monosaccharide Composition of Mucus Glycoprotein Product from *M. glacialis*

The monosaccharide compositions for purified and partially purified samples from *M. glacialis* are shown herein. For both the partially purified and pure samples over 70% of the material consists of glucose, galactose, N-acetyl galactosamine (GalNAc) and N-acetyl glucosamine (GlcNAc). Purification reduces the proportion of GalNAc (by more than half) and also of GlcNAc, but increases the proportions of galactose and glucose present. Minor components of the mixture are arabinose, mannose, fucose and xylose. The proportions of arabinose and mannose increase on purification, each to about 8% of the total in the purified preparation. No sialic acids or uronic acids were found. The composition of monosaccharides in all the samples is consistent with the presence of a mucin type glycoprotein.

NMR Spectroscopy of Partially Purified Glycoprotein Product From *M. glacialis*

The proton spectrum of the *M. glacialis* glycoprotein at 500 MHz is shown in the accompanying figures. Signals attributable to both carbohydrate and peptide are present, and the distinctive acetyl methyl signal at 2.05 ppm is consistent with the high proportion of GalNAc and GlcNAc identified by monosaccharide analysis. Anomeric resonances from monosaccharide residues are seen between 4.4 and 5.2 ppm. A group of three sharp signals between 5.0 and 5.2 ppm is attributable to $\alpha$-anomeric protons, with signals between 4.4 and 4.8 ppm from $\beta$-anomers.

Infra-red spectra of mucus glycoproteins

FTIR analysis of partially purified mucus glycoproteins produced characteristic spectra with many features shared between the three species. Comparison of these spectra with spectra taken from mammalian glycosaminoglycans and mucin suggests that the compounds are mucin type glycoproteins. Tentative peak assignments were made (table 4) using published data[24], these are peaks which appear to be characteristic of mucin-type glycoproteins although some of them are shared with glycosaminoglycans.

Effect of mucus glycoproteins on bacterial adhesion

Initial studies of bacterial adhesion were made under flow using the real-time adhesion apparatus. These studies indicated that mucus glycoproteins from M glacialis were effective in inhibiting adhesion to glass slides. Further real time studies demonstrated that *M. glacialis* mucus glycoprotein causes bacteria to stick together in clumps. Without wishing to be bound by theory, this clump formation may provide a mechanistic explanation of the anti-adhesive properties of the product according to the invention.

Subsequent studies of static bacterial adhesion using radiolabelled bacteria indicated that adhesion to tissue culture plastic was inhibited by up to −52.8% (±23.7, SD, n=5) by *M. glacialis* mucus glycoprotein product Porcine dermatan sulfate enhanced bacterial adhesion in a dose-dependent manner, reaching a maximum increase of 67.9% (±37.9, SD,n=5).

Effect of mucus glycoprotein products on cellular adhesion

Partially purified mucus glycoprotein product from all species studied (see above) were not cytotoxic and inhibited neutrophil adhesion in a dose dependent manner. The glycoprotein from *M. glacialis* inhibited leukocyte adhesion by up to 67.6% (±15.6, SD, n=6), glycoprotein from *P. pulvillus* inhibited adhesion by up to 43.9% (±19.7, SD, n=4), and glycoprotein from *O. nigra* inhibited adhesion by up to 47.2% (±10.9, SD, n=4). The sample from *M. glacialis* was a more potent inhibitor of leukocyte adhesion than mammalian heparin.

None of the mucus glycoproteins had any measurable anticoagulant activity.

The glycoprotein product from *M. glacialis* and *O. nigra* blocks adhesion of bacteria in a static adhesion assay. Furthermore, when we examine the bacteria used for real-time studies they are seen to have formed large aggregates, presumably due to adhesion to glycoprotein molecules. These results demonstrate that the mucus glycoprotein products are capable of blocking adhesion sites.

SUMMARY

The protective function of secreted and membrane-bound mucins is widely accepted in mammalian biology[7;40;58] Abnormalities of mucus glycoprotein production or structure are also implicated in the pathology of many diseases including cystic fibrosis[7], inflammatory bowel disease, Crohn's disease, ulcerative colitis[47], bronchitis, asthma[59], and many carcinomas [7;60]. It is envisaged that the non-mammalian mucin products disclosed herein have therapeutic potential to treat these and related inflammatory disorders by blocking the adhesion of leukocytes.

OVERALL SUMMARY

As disclosed herein, the present invention relates to a product capable of having one or more properties selected from anti-fouling properties, anti-adhesive properties, anti-inflammatory properties, wherein said product is obtainable from starfish.

REFERENCES TO EXAMPLE 7

1. WAHL, M. (1989). *Marine Ecology Progress Series* 58 175–189.
2. ABARZUA, S. & JAKUBOWSKI, S. (1995). *Marine Ecology Progress Series* 123 301–312.
3. BEVILACQUA, M. P., NELSON, R. M., MANNORI, G. & CECCONI, O. (1994). Endothelial-leukocyte adhesion molecules in human disease. *Annu. Rev. Med.* 45 361–378.
4. KLEIN, N. J., SHENNAN, G. I., HEYDERMAN, R. S. & LEVIN, M. (1992). Alteration in glycosaminoglycan metabolism and surface charge on human umbilical vein endothelial cells induced by cytokines, endotoxin and neutrophils. *J. Cell Science* 102 821–832.
5. VLODAVSKY, I., ELDOR, A., HAIMOVITZ-FRIEDMAN, A., MATZNER, Y., ISHAI-MICHAELI, R., LIDER, O., NAPARSTEK, Y., COHEN, I. R. & FUKS, Z. (1992). Expression of heparinase by platelets and circulating cells of the immune system: Possible involvment in diapedesis and extravasation. *Invasion Metastasis* 12 112–127.
6. MURCH, S. H., MacDONALD, T. T., WALKER-SMITH, J. A., LEVIN, M., LIONETTI, P. & KLEIN, N. J. (1993). Disruption of sulphated glycosaminoglycans in intestinal inflammation. *Lancet* 341 711–714.
7. JAQUES, L. B. (1979). Heparins—anionic polyelectrolyte drugs. *Pharmacol. Rev.* 31 99–167.
8. TYRRELL, D. J., HORNE, A. P., HOLME, K. R., PREUSS, J. M. H. & PAGE, C. P. (1999). Heparin in inflammation: Potential therapeutic applications beyond anticoagulation. *Adv. Pharmacol.* 46 151–208.
9. SILVESTRO, L., VIANO, I., MACARIO, M., COLANGELO, D., MONTRUCCHIO, G., PANICO, S. & FANTOZZI, R. (1994). Effects of heparin and its desulfated derivatives on leukocyte-endothelial adhesion. *Sem Thromb. Haemost.* 20 254–258.
10. XIE, X., THORLACIUS, H., RAUD, J., HEDQVIST, P. & LINDBOM, L. (1997). Inhibitory effect of locally administered heparin on leukocyte rolling and chemoattractant-induced firm adhesion in rat mesenteric venules in vivo. *Br. J. Pharmacol.* 122 906–910.
11. BAZZONI, G., NUÑEZ, A. B., MASCELLANI, G., BIANCHINI, P., DEJANA, E. & DEL MASCHIO, A. (1993). Effect of heparin, dermatan sulfate, and related oligo-derivatives on human polymorphonuclear leukocyte functions. *J. Lab. Clin. Med.* 121 268–275.
12. LEVER, R., HOULT, J. R. S & PAGE, C. P. (2000). The effects of heparin and related molecules upon the adhesion of human polymorphonuclear leucocytes to vascular endothelium in vitro. *Br. J. Pharmacol.* 129 533–540.
13. TANGELDER, G. J. & ARFORS, K-E. (1991). Inhibition of leukocyte rolling in venules by protamine and sulfated polysaccharides. *Blood* 7 1565–1571.
14. LEY, K., CERRITO, M. & ARFORS, K-E. (1991). Sulfated polysaccharides inhibit leukocyte rolling in rabbit mesentery venules. *Am. J. Physiol.* 260H1667–1673.
15. KRAEMER, P. M. (1977). Heparin releases heparan sulfate from the cell surface. *Biochem. Biophys. Res. Comm.*
16. PARSONS, C. L., BOYCHUK, D., JONES, S., HURST, R. & CALLAHAN, H. (1990). Bladder surface glycosaminoglycans: An epithelial permeability barrier. *J. Urology* 143 139–142.
17. PARSONS, C. L., STAUFFER, C. & SCHMIDT, J. D. (1980). Bladder-surface glycosaminoglycans: An efficient mechanism of environmental adaptation. *Science* 208 605–607.
18. PARSONS, C. L. (1997). Epithelial coating techniques in the treatment of interstitial cystitis. *Urology* 49 100–104.

24. McKENZIE, J. D. (1988). *Cell and Tissue Research* 251 387–397.

REFERENCES TO EXAMPLE 8

1. Chaet, A. B. and Philpott, D. E. (1964) *Journal of Ultrastructure Research* 11, 354–362
2. Alfred B. Chaet (1962) *Ann. N.Y. Acad. Sci.* 921–929
3. Thomas, L. A. and Hermans, C. O. (1985) *Reference: Biol, Bull* 169, 675–688
4. McKenzie, J. D. and Grigovala, I. V. (1996) *Biofouling* 10, 261–272
5. Fontaine, A. R. (1964) *Journal of the Marine Biology Association of the United Kingdom* 44,145–162
6. Carlstedt, I. and Davies, J. R. (1997) *Biochem. Soc. Trans.* 25, 214–219
7. Strous, G. J. and Dekker, J. (1992) *Crit. Rev. Biochem. Mol. Biol.* 27, 57–92
8. Hardstaff, W. R. and Fosang, A. J. (1992) *FASEB J.* 6, 861–870
9. Kim, Y.-J., Grodzinsky, A. J., and Plaas, A. H. K. (1996) *Arch. Biochem. Biophys.* 328, 331–340
10. Hook, M., Kjellen, L., Johansson, S., and Robinson, J. (1984) *Annu. Rev. Biochem.* 53, 847–869
11. Wahl, M. (1989) *Marine Ecology Progress Series* 58, 175–189
12. Abarzua, S. and Jakubowski, S. (1995) *Marine Ecology Progress Series* 123, 301–312
13. Pavao, M. S. G., Mourao, P. A. S., Mulloy, B., and Toliefsen, D. M. (1995) *JBC* 270, 31027–31036
14. Mourao, P. A. S., Pavao, M. S. G., Mulloy, B., and Wait, R. (1997) *Carbohydr. Res.* 828,
15. Pavao, M. S. G., Aiello, K. R. M., Werneck, C. C., Silva, L. C. F., Valente, P., Mulloy, B., Colwell, N. S., Tollefsen, D. M., and Mourao, P. A. S. (1998) *Journal of Biological Chemistry* 273, 27848–27857
16. Meikle, P., Richards, G. N., and Yellowlees, D. (1987) *Journal of Biological Chemistry* 262, 16941–16947
17. Farndale, R. W., Buttle, D. J., and Barrett, A. J. (1986) *Biochim. Biophys. Acta* 883, 171–177
18. Bitter, T. and Muir, H. M. (1962) *Analytical Biochemistry* 4, 330–334
19. Rondle, C. J. M. and Morgan, W. T. J. (1955) *Biochem. J.* 61, 586–589
20. Ferguson, M. A. J. (1993) GPI membrane anchors: isolation and analysis. In Minoru Fukuda and Akira Kobata, editors. *Glycobiology. A practical approach*, Oxford University Press, Oxford
21. S. Inoue and M. Miyawaki (1973) *Biochim. Biophys. Acta* 320, 73–78
22. Usami, S., Chen, H.-H., Zhao, Y., Chen, S., and Skalak, R. (1993) *Ann. Biomed. Eng.* 21, 77–83
23. Kyan-Aung, U., Haskard, D. O., and Lee, T. H. (1991) *American Journal of Respiratory Cellular and Molecular Biology* 5, 445–450
24. Brandenburg, K. and Seydel, U. (1996) Fourier Transform Infrared Spectroscopy of Cell Surface Polysaccharides. In Mantsch, H. H. and Chapman, D., editors. *Infrared Spectroscopy of Biomolecules*, Kiley-Liss, Inc.,
25. Chen, Q., Barragan, A., Fernandez, V., Sundstrom, A., Schlichtherie, M., Sahlen, A., Carlson, J., Datta, S., and Wahlgren, M. (1998) *J. Exp. Med.* 187, 15–23.
26. Misevic, G. N. and Burger, M. M. (1993) Journal of Biological Chemistry 268, 4922–4929
27. Wight, T. N., Kinsella, M. G., and Qwarnstrom, E. E. (1992) *Curr. Opp. Cell Biol.* 4, 793–801
28. Woods, A. and Couchman, J. R. (1998) *Trends in Cell Biology* 8, 189–192
29. Liu, S., Hoke, D., Julian, J., and Carson, D. D. (1997) *The Journal of Biological Chemistry* 272, 25856–25862
30. Jones, R. (1991) *Development* 111, 1155–1163
31. Masahito, Y. (1997) *Trends in Glycoscience and Glycotechnology* 9(suppl), S25–S28
32. Bidanset, D. J., LeBaron, R., Rosenberg, L., Murphy-Ulrich, J. E., and Hook, M. (1992) *The Journal of Cell Biology* 118, 1523–1531
33. Wesseling, J., van der Valk, S. W., Vos, H. A., Sonnenberg, A., and Hilkens, J. (1995) *Journal of Cell Biology* 129, 255–265
34. Yamada, Y. and Olden, K. (1978) *Nature* 275, 179–184
35. Suzuki, T., Kurokawa, T., and Asashima, M. (1994) *Fish Physiology and Biochemistry* 13, 343–352
36. Spiegel, E., Howard, L., and Speigel, M. (1989) *J. Morphol.* 199, 71–92
37. Emak, A. V. and Odinstova, N. A. (1996) *Biologiya Morya* 22, 371–377
38. Kinoshita, S. (1971) *Experimental Cell Research* 64, 403–411
39. Kinoshita, S. (1974) *Experimental Cell Research* 85, 31–40
40. Carson, D. D., DeSouza, M. M., and Regisford, E. G. C. (1998) *Bio Essays* 20, 577–583
41. Har-El, R. and Tanzer, M. L. (1993) *FASEB J.* 7, 1115–1123
42. Morris, P. J. (1993) *Evolution* 47, 152–165
43. Stromblad, S. and Cheresh, D. A. (1996) *Trends in Cell Biology* 6, 462–468
44. Margolis, R. U. and Margolis, R. K. (1997) *Cell Tissue Res.* 290, 343–348
45. Shworak, N. W. and Rosenberg, R. D. (1998) *Trends in Glycoscience and Glycotechnology* 10, 175–192
46. Small, D. H., Williamson, T., Reed, G., Clarris, H., Beyreuther, K., Masters, C. L., and Nurcombe, V. (1996) *Annals of the New York Academy of Sciences* 777, 316–321
47. Corfield, A. P. and Warren, B. F. (1996) *J. Pathol.* 180, 8–17
48. Spillmann, D. and Burger, M. M. (1996) *J. Cell Biochem.* 61, 562–568
49. Jacquet, A., Haumont, M., Chellun, D., Massaer, M., Tufaro, F., Bollen, A., and Jacobs, P. (1998) *Virus Res.* 53, 197–207
50. Alvarez-Dominguez, C., Vazquez-Boland, J.-A., Carrasco-Marin, E., Lopez-Mato, P., and Leyva-Cobian, F. (1997) *Infect. Immun.* 65, 78–88
51. Lowe, D. C., Esko, J. D., and Mosser, D. M. (1993) *The Journal of Cell Biology* 123, 759
52. Leong, J. M., Wang, H., Magoun, L., Field, J. A., Morrissey, P. E., Robbins, D., Tatro, J. B., Coburn, J., and Parveen, N. (1998) *Infect. Immun.* 66, 994–999
53. Chmiela, M., PaziakDomanska, B., Rudnicka, W., and Wadstorm, T. (1995) *APMIS* 103, 469474
54. Kadipasaoglu, K. A., Bilge, F. H., and Baier, R. E. (1993) *J. Biomed. Mater. Res.* 27, 207–216
55. Perez-Vilar, J. and Hill, R. (1999) *Journal of Biological Chemistry* 277, 31751–31754
56. Berg, E. L., McEvoy, L. M., Berlin, C., Bergatze, R. F., and Butcher, E. C. (1993) *Nature* 366, 695–698
57. Shimizu, Y. and Shaw, S. (1993) *Nature* 366, 630–631
58. Van Klinken, B. J.-W., Dekker, J., Buller, H. A., and Einerhand, A. W. C. (1995) *American Journal of Physiology* 269, G613–G627

59. Rose, M. C. (1992) *American Journal of Physiology* 263, L413–L429
60. Makiguchi, Y., Hinoda, Y., and Imai, K. (1996) *Jpn. J. Cancer Res.* 87, 505–511

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A product capable of having anti-inflammatory properties,
   wherein said product is obtainable from starfish,
   wherein said product is glycoprotein,
   wherein said glycoprotein has a molecular weight of about 1,100 kDa as measured by 3% polyacrylamide gel electrophoresis,
   wherein the glycoprotein exhibits at least one characteristic selected from the group consisting of:
   a) sensitivity to the action of chondroitinase ABC I,
   b) sensitivity to the action of N-glycanase,
   c) resistance to the action of chondroitinases ACI and B,
   d) resistance to the action of proteinase K,
   e) resistance to the action of papain, and
   f) sensitivity to the action of neuraminidase;
   and the product has:
   a characteristic nuclear magnetic resonance proton spectrum at 500 MHz as shown in FIG. 1 of the drawings; and
   a characteristic Fourier transform infra-red spectrum as shown in FIG. 2 of the drawings.

2. A product according to claim 1 wherein said product is obtainable from the mucus secretions of the starfish.

3. A product according to claim 1 wherein the starfish is *Marthasterias glacialis*.

4. A product according to claim 1, said product not having significant anticoagulant properties.

5. A method for the preparation of a product capable of having anti-inflammatory properties, wherein said product is obtainable from starfish, wherein said product is glycoprotein, wherein said glycoprotein has a molecular weight of about 1,100 kDa as measured by 3% polyacrylamide gel electrophoresis, wherein the glycoprotein exhibits at least one characteristic selected from the group consisting of:
   a) sensitivity to the action of chondroitinase ABC I,
   b) sensitivity to the action of N-glycanase,
   c) resistance to the action of chondroitinases ACI and B,
   d) resistance to the action of proteinase K,
   e) resistance to the action of papain, and
   f) sensitivity to the action of neuramimidase,
said method comprising:
   a) collecting mucus from Marthasterias glacialis,
   b) removing particulate material by centrifugation,
   c) subjecting the supernatant to column chromatography,
   d) eluting the product from the chromatography column of (c), and
   e) optionally dialysing said eluted product against distilled water.

6. A pharmaceutical comprising the product of claim 1.

7. A composition comprising a glycoprotein obtainable from the mucus secretions of *Marthasterias glacialis* which exhibits a molecular weight of about 1,100 kDa as measured by 3% polyacrylamide gel electrophoresis, and is sensitive to the action of chondroitinase ABC I, sensitive to the action of N-glycanase, sensitive to the action of neuramimidase, resistant to the action of chondroitinases ACI and B, resistant to the action of proteinase K, and resistant to the action of papain and which has a characteristic nuclear magnetic resonance proton spectrum at 500 MHz as shown in FIG. 1 of the drawings; and a characteristic Fourier transform infra-red spectrum as shown in FIG. 2 of the drawings.

* * * * *